United States Patent [19]

Wickham et al.

[11] Patent Number: 5,962,311
[45] Date of Patent: Oct. 5, 1999

[54] SHORT-SHAFTED ADENOVIRAL FIBER AND ITS USE

[75] Inventors: Thomas J. Wickham, Potomac; Petrus W. Roelvink, Olney; Imre Kovesdi, Rockville, all of Md.

[73] Assignee: GenVec, Inc., Rockville, Md.

[21] Appl. No.: 08/700,846

[22] Filed: Aug. 21, 1996

Related U.S. Application Data

[63] Continuation-in-part of application No. 08/634,060, Apr. 17, 1996, Pat. No. 5,712,136, which is a continuation-in-part of application No. 08/303,162, Sep. 8, 1994, Pat. No. 5,559,099.

[51] Int. Cl.[6] .............................. C12N 15/86; C12N 7/01
[52] U.S. Cl. .................. 435/320.1; 435/69.7; 435/235.1
[58] Field of Search .............................. 514/44; 435/69.7, 435/5, 172.1, 235.1, 320.1, 172.3; 424/93.2; 530/350

[56] References Cited

U.S. PATENT DOCUMENTS

| | | | |
|---|---|---|---|
| 4,593,002 | 6/1986 | Dulbecco | 435/172.3 |
| 5,223,409 | 6/1993 | Ladner et al. | 435/69.7 |
| 5,403,484 | 4/1995 | Ladner et al. | 435/235.1 |
| 5,521,291 | 5/1996 | Curiel et al. | 530/391.7 |
| 5,543,328 | 8/1996 | McClelland et al. | 435/320.1 |
| 5,547,932 | 8/1996 | Curiel et al. | 435/65 |
| 5,559,099 | 9/1996 | Wickham et al. | 514/44 |
| 5,571,698 | 11/1996 | Ladner et al. | 435/69.7 |

FOREIGN PATENT DOCUMENTS

| | | |
|---|---|---|
| WO 94/10323 | 5/1994 | WIPO . |
| WO 95/17832 | 8/1994 | WIPO . |
| WO 95/05201 | 2/1995 | WIPO . |
| WO 95/26412 | 10/1995 | WIPO . |

OTHER PUBLICATIONS

Gall et al., *Journal of Virology*, 70, 2116–2123 (1996).
Albiges–Rizo et al., *J. Biolog. Chem.*, 266, 3961–3967 (1991).
Bai et al, *J. Virol*, 67, 5198–5205 (1993).
Boursnell et al., *Gene*, 13, 311–317 (1981).
Caillet–Boudin et al, *J. Mol. Biol.*, 217, 477–486 (1991).
Crystal, *Science*, 270, 404–410 (1995).
Etienne–Julan et al., *J. Gen Virol.*, 73, 3251–3255 (1992).
Falgout et al., *J. Virol.*, 62, 622–625 (1992).
Henry et al., *J. Virol*, 68 (8), 5239–5246 (1994).
Hong et al., *Virology*, 185, 758–767 (1991).
Karyan et al., *Virology*, 202, 782–785 (1994).
Michael et al., *J. Biolog. Chem.*, 268, 6866–6869 (1993).
Michael et al., *Gene Therapy*, 2, 660–668 (1995).
Michael et al., "Addition of Short Peptide Ligand Sequences to the Adenovirus Fiber Protein," presented at Adenovirus Workshop: St. Andrews University, p. 52 (Jul. 13–15, 1995).
Miller et al., *FASEB J.*, 9, 190–199 (1995).
Nemerow et al., *In Biology of Vitronectins and their Receptors* (Preissner et al., eds.), 177–184 (Elsevier Science Publishers, (1993).
Nemerow et al., *Trends in Cell Biology*, 4, 52–55 (1994).
Novelli et al., *Virology*, 185, 365–376 (1991).
Peteranderl et al., *Biochemistry*, 31, 12272–12276 (1992).
Signas et al., *J. Virol.*, 53, 672–678 (1985).
Wickham et al., *Cell*, 73, 309–319 (1993).
Wickham et al., *Gene Therapy*, 2, 750–756 (1995).
Wickham et al., *J. Cell Biol.*, 127, 257–264 (1994).
Wickham et al., *J. Virol.*, 70, 6831–6838 (1996).
Xia et al., *Structure*, 2, 1259–1270 (1994).

*Primary Examiner*—David Guzo
*Assistant Examiner*—Matthew Latimer
*Attorney, Agent, or Firm*—Leydig, Voit & Mayer, Ltd.

[57] ABSTRACT

The present invention provides a short-shafted adenoviral fiber, a recombinant adenovirus comprising a short-shafted fiber, a vector comprising a short-shafted adenoviral fiber gene, and a method of targeting attachment of a short-shafted recombinant adenovirus to a cell so as to effect entry of the short-shafted recombinant adenovirus into the cell.

60 Claims, 18 Drawing Sheets

SHORT-SHAFTED ADENOVIRAL FIBER AND ITS USE

RELATED APPLICATIONS

This is a continuation-in-part application of co-pending U.S. patent application Ser. No. 08/634,060, filed Apr. 17, 1996 now U.S. Pat. No. 5,712,136, which is a continuation-in-part of U.S. patent application Ser. No. 08/303,162, filed Sep. 8, 1994 now U.S. Pat. No. 5,559,099.

TECHNICAL FIELD OF THE INVENTION

The present invention pertains to a short-shafted adenoviral fiber, a recombinant adenovirus comprising a short-shafted fiber, a vector comprising a short-shafted adenoviral fiber gene, and a method of targeting attachment of a short-shafted recombinant adenovirus to a cell so as to effect entry of the short-shafted recombinant adenovirus into the cell.

BACKGROUND OF THE INVENTION

Adenoviruses belong to the family Adenoviridae, which is divided into two genera, namely Mastadenovirus and Aviadenovirus (Horwitz, Shenk and Murphy, individually, *In Virology*, 3rd ed., Fields et al., eds., pages 2149–2171, 2111–2148, and 15–57, respectively (Raven Press, New York (1996)). Human adenoviruses are classified into six subgroups, namely A through F, based on hemagglutination patterns of erythrocytes from diverse animal species, and are further classified into over 49 serotypes (Horwitz et al., supra; and Schnurr et al., *Intervirol.*, 36, 79–83 (1993)).

Adenoviruses are nonenveloped, regular icosahedrons of about 65 to 80 nm in diameter. The adenoviral capsid comprises 252 capsomeres, of which 240 are hexons and 12 are pentons. The hexons and pentons are derived from three different viral polypeptides (Maizel et al., *Virology*, 36, 115–125 (1968); Weber et al., *Virology*, 76, 709–724 (1977)). The hexon comprises three identical polypeptides of 967 amino acids each, namely polypeptide II (Roberts et al., *Science*, 232, 1148–1151 (1986)). The penton comprises a penton base, which provides a point of attachment to the capsid, and a trimeric fiber protein, which is noncovalently bound to and projects from the penton base.

The penton base, itself, is a ring-shaped complex comprising five identical proteinaceous subunits of polypeptide III (571 amino acids) (Boudin et al., *Virology*, 92, 125–138 (1979)). The penton base sequence is conserved among the various serotypes of adenovirus that have been sequenced (Neumann et al., *Gene*, 69, 153–157 (1988)).

The fiber protein comprises three identical proteinaceous subunits of polypeptide IV (582 amino acids) and comprises a tail, a shaft and a knob (Devaux et al., *J. Molec. Biol.*, 215, 567–588 (1990)). The fiber shaft comprises repeats of 15 amino acids, which are believed to form two alternating β-strands and β-bends (Green et al., *EMBO J.*, 2, 1357–1365 (1983)). The overall length of the fiber shaft and the number of 15 amino acid repeats varies between adenoviral serotypes. For example, the Ad2 fiber shaft is 37 nm long and comprises 22 repeats, whereas the Ad3 fiber is 11 nm long and comprises 6 repeats. Sequencing of over ten fiber proteins from different adenoviral serotypes has revealed a greater sequence diversity than that observed among other adenoviral proteins. For example, the knob regions of the fiber proteins from the closely related Ad2 and Ad5 serotypes are only 63% similar at the amino acid level (Chroboczek et al., *Virology*, 186, 280–285 (1992)), whereas their penton base sequences are 99% identical.

Ad2 and Ad5 fiber proteins, however, both likely bind to the same cellular receptor, since they cross-block each other's binding. In contrast, Ad2 and Ad3 fibers are only 20% identical (Signas et al., *J. Virol.*, 53, 672–678 (1985)) and bind to different receptors (Defer et al., *J. Virol.*, 64(8), 3661–3673 (1990)).

Other proteins, namely proteins IX, VI, and IIIa also are present in the adenoviral capsid. These proteins are believed to stabilize the viral capsid (Stewart et al., *Cell*, 67, 145–154 (1991); Stewart et al., *EMBO J.*, 12(7), 2589–2599 (1993)).

An adenovirus, namely serotype 2 (Ad2), has been shown to use the fiber and the penton base to interact with distinct cellular receptors to attach to and efficiently infect a cell (Wickham et al., *Cell*, 73, 309–319 (1993)). First, the virus uses a receptor binding domain localized in the fiber knob (Henry et al., *J. Virol.*, 68(8), 5239–5246 (1994)) to attach to an, as yet, unidentified cell-surface receptor (Phillipson et al., *J. Virol.*, 2, 1064–1075 (1968); Wickham et al., *Cell*, 73, 309–319 (1993); Svensson et al., *J. Virol.*, 38, 70–81 (1981); Hennache et al., *Biochem. J.*, 166, 237–247 (1977); Defer et al. (1990), supra; and DiGuilmi et al., *Virus Res.*, 38, 71–81 (1995)). Then, following viral attachment, the penton base binds to a specific member of a family of heterodimeric cell-surface receptors called integrins. For the Ad2 and Ad5 serotypes, which possess the long-shafted fibers, the penton base is not significantly involved in viral attachment to host cells (Wickham et al. (1993), supra).

The specificity with which an adenoviral penton base binds to an integrin is a function of the paired α and β subunits of the integrin. For instance, the Ad2 penton base binds to integrins $\alpha_v\beta_3$ and $\alpha_v\beta_5$ (Wickham et al. (1993), supra; Nemerow et al., *In Biology of Vitronectins and their Receptors*, Preissner et al. (eds.), pages 177–184 (Elsevier Science Publishers (1993)); and Varga et al., *J. Virol.*, 65, 6061–6070 (1991)). Some integrins, such as the $\alpha_v$ integrins, are present on the surface of nearly all cells, except for unstimulated hematopoietic cells (Gladson et al., *In Integrins*, Y. Takada (ed.), pages 83–99 (CRC Press, Boca Raton, Fla. (1994)), whereas other integrins have a narrower tissue distribution. In particular, $\beta_2$ integrins are present only on leukocytes, such as neutrophils and macrophages, $\alpha_4$ integrins are present only on lymphocytes and fibroblasts, and the $\alpha_{IIb}\beta_3$ integrin is present only on platelets and megakaryocytes. The integrin subunit complement of a cell, therefore, in some sense limits the infectability of that cell by different serotypes of adenovirus.

Most integrins recognize short linear stretches of amino acids in a ligand, such as the tripeptide RGD (i.e., Arg Gly Asp), which is found in the majority of extracellular matrix ligands. The integrin $\alpha_{IIb}\beta_3$ binds fibrinogen via the amino acid sequence KQAGD (i.e., Lys Gln Ala Gly Asp; SEQ ID NO: 1) (Kloczewiak et al., *Biochemistry*, 23, 1767–1774 (1984)), and $\alpha_4\beta_1$ binds fibronectin via the core sequence EILDV (i.e., Glu Ile Leu Asp Val; SEQ ID NO: 2) (Komoriya et al., *J. Biol. Chem.*, 266, 15075–15079 (1991)). Another structural motif, NPXY (i.e., Asn Pro Xaa Tyr; SEQ ID NO: 3), which is present in the β subunits of $\alpha_v$-containing integrins, also has been shown to be important for integrin-mediated internalization (Suzuki et al., *PNAS (USA)*, 87, 5354 (1990)).

It appears that the RGD tripeptide also functions in the interaction of adenoviral penton base with $\alpha_v$ integrins. Exogenously added RGD peptides block the penton base from binding to cells (Wickham et al. (1993), supra), and adenoviruses with point mutations in the RGD sequence of the penton base are restricted in their ability to infect cells (Bai et al., *J. Virol.*, 67, 5198–5205 (1993)).

The RGD tripeptide sequence is present in the hypervariable regions of Ad2 and Ad5 (both are subgroup C) penton bases, which are identical in the region of the RGD tripeptide sequence. Secondary structural analysis of the hypervariable regions of the RGD-containing penton bases of Ad2, Ad5, and Ad12 (subgroup A) predicts that, in each case, the RGD motif is flanked by α-helices, which are believed to form the spikes seen in cryo-electron micrographic (cryo-EM) images of the Ad2 penton base (Stewart et al., *EMBO J.*, 12(7), 2589–2599 (1993)). The RGD tripeptide also is present in the penton base of Ad3 (subgroup B, which strongly hemagglutinates rhesus erythrocytes but not those of rat) and Ad4 (subgroup E).

Once Ad2 or Ad5 attaches to a cell via its fiber, it undergoes receptor-mediated internalization into clathrin-coated endocytic vesicles by penton base binding to integrins. The Ad2 or Ad5 (subgroup C) penton base is not significantly involved in viral attachment to the host cell (Wickham et al. (1993), supra), presumably due to the length of their fiber shafts (37 nm), which may sterically block a primary attachment event to $\alpha_v$ integrins. Ultimately, the viral particles are transported to the nuclear pore complex of the cell, where the viral genome enters the nucleus, thereby initiating infection.

The ability of adenovirus to enter cells efficiently has allowed the adenoviral-mediated targeted transfer of one or more recombinant genes to diseased cells or tissue in need of treatment. In fact, adenoviral vectors are preferred over other vectors commonly employed for gene therapy (e.g., retroviral vectors), since adenoviral vectors can be produced in high titers (i.e., up to about $10^{13}$ viral particles/ml) and they efficiently transfer genes to nonreplicating, as well as replicating, cells (see, for example, review by Crystal, *Science*, 270, 404–410 (1995)). Adenoviral vectors are especially preferred for somatic gene therapy of the lungs, given their normal tropism for the respiratory epithelium.

Other advantages that accompany the use of adenoviruses as vectors for gene therapy include: (1) the rare observance of recombination; (2) the absence of an ostensible correlation of any human malignancy with adenoviral infection, despite the common occurrence of infection; (3) the adenoviral genome (which is comprised of linear, double-stranded DNA) can be manipulated to carry up to about 7.5 kb of exogenous DNA, and longer DNA sequences can potentially be carried into a cell, for instance, by attachment to the adenoviral capsid (Curiel et al., *Human Gene Therapy*, 3, 147–154 (1992)); (4) an adenovirus is unlikely to interfere with normal cell function since the vector commands expression of its encoded sequences in an epichromosomal fashion; and (5) live adenovirus has been safely used as a human vaccine for many years.

A drawback to the use of adenovirus in gene therapy, however, is that all cells that comprise receptors for the adenoviral fiber and penton base will internalize the adenovirus, and, consequently, the gene(s) being administered—not just the cells in need of therapeutic treatment. Also, cells that lack either the fiber receptor or the penton base receptor, e.g., integrin, will be impaired in adenoviral mediated gene delivery (Silver et al., *Virology*, 165, 377–387 (1988); Horvath et al., *J. Virol.*, 62, 341–345 (1988); and Huang et al., *J. Virol.*, 69, 2257–2263 (1995)). Similarly, other cells, which appear to lack an adenoviral fiber receptor, are transduced by adenovirus, if at all, with a very low efficiency (Curiel et al. (1992), supra; Cotten et al., *PNAS* (*USA*), 87, 4033–4037 (1990); Wattel et al., *Leukemia*, 10, 171–174 (1996)). Accordingly, limiting adenoviral entry to specific cells and/or expanding the repertoire of cells amenable to adenovirus-mediated gene therapy would constitute a substantial improvement over the current technology. Such truly "targeted" adenoviral gene delivery also could potentially reduce the amount of adenoviral vector that is necessary to obtain gene expression in the targeted cells and, thus, potentially reduce side effects and complications associated with an increased dose of adenovirus.

In efforts to achieve cell targeting, adenovirus has been employed essentially as an endosomolytic agent in the transfer into a cell of plasmid DNA, which contains a marker gene and is complexed and condensed with polylysine covalently linked to a cell-binding ligand, such as transferrin (Cotten et al., *PNAS* (*USA*), 89, 6094–6098 (1992); and Curiel et al., *PNAS* (*USA*), 88, 8850–8854 (1991)). It has been demonstrated that coupling of the transferrin-polylysine/DNA complex and adenovirus (e.g., by means of an adenovirus-directed antibody, with transglutaminase, or via a biotin/streptavidin bridge) substantially enhances gene transfer (Wagner et al., *PNAS* (*USA*), 89, 6099–6103 (1992)). However, these approaches are somewhat less than desirable in that they require the ligation of the ligand, such as transferrin, with polylysine, and the advance preparation of the transferrin-polylysine DNA complexes. Moreover, the complexes formed with adenovirus could be endocytosed by binding either to cellular adenoviral receptors or to transferrin receptors. Additionally, polylysine, by itself, is capable of binding to cells, thereby interfering with the specificity of this approach.

In order to circumvent such non-specific binding of the adenovirus, the adenoviral fiber has been modified, either by incorporation of sequences for a ligand to a cell surface receptor or sequences that allow binding to a bispecific antibody (i.e., a molecule with one end having specificity for the fiber, and the other end having specificity for a cell surface receptor) (PCT international patent application no. WO 95/26412 (the '412 application); Watkins et al., "Targeting Adenovirus-Mediated Gene Delivery with Recombinant Antibodies," Abst. No. 336). In both cases, the typical fiber/cell surface receptor interactions are abrogated, and the adenovirus is redirected to a new cell surface receptor by means of its fiber. Some downfalls associated with the approach of the '412 application, which calls for modification of the fiber, are that such fiber modifications can require the need for different cell lines (i.e., cell lines having the receptor for which the modified virus is now targeted) to propagate the virus, and/or a different means of cell delivery (e.g., liposome-mediated delivery) to introduce adenovirus intracellularly. Moreover, the approaches of Watkins et al. and the '412 application appear to be limited to the use of the adenoviral fiber in cell targeting.

Another approach to targeted gene delivery involves administering a targeting element coupled to a first molecule of a high affinity binding pair, wherein the targeting element is capable of specifically binding to a selected cell type (PCT international patent application no. WO 95/31566). Then, a gene delivery vehicle coupled to a second molecule of the high affinity binding pair is administered, wherein the second molecule is capable of specifically binding to the first molecule, such that the gene delivery vehicle is targeted to the selected cell type. The sequential administration of the various components is probably done to prevent agglomeration of the vector particles, e.g., in cases where the targeting element is multivalent for the domain that recognizes the vector, which would reduce transduction efficiency. However, such sequential administration is disadvantageous, since it allows for internalization of the targeting element before it can complex with the vector. Furthermore, internalization of the preadministered targeting element clears the receptor from the cell surface, thereby preventing efficient targeting of the complexed targeting element and vector, and also potentially leading to impairment of the cell processes controlled by the receptors. Moreover, such premature internalization would necessitate the use of relatively high levels of the targeting element.

The present invention seeks to overcome many of the problems of the aforesaid approaches to recombinant adenoviral gene therapy. Accordingly, it is an object of the present invention to provide a method of targeting attachment of an adenovirus to a cell for cell entry, as well as recombinant adenovirus, vectors and other constituents for carrying out the method. These and other objects and advantages of the present invention, as well as additional inventive features, will be apparent from the following detailed description.

BRIEF SUMMARY OF THE INVENTION

The present invention provides a short-shafted adenoviral fiber as defined herein, a recombinant adenovirus comprising a short-shafted fiber, a recombinant baculovirus comprising a short-shafted adenoviral fiber gene, a vector, in particular a viral transfer vector, preferably an adenoviral transfer vector, or a prokaryotic or eukaryotic expression vector, comprising a short-shafted adenoviral fiber gene, and a method of targeting attachment of a short-shafted recombinant adenovirus to a cell so as to effect entry of the short-shafted recombinant adenovirus into the cell. The method reduces the level or efficiency of adenoviral fiber binding to its cell-surface receptor and increases adenoviral penton base binding to its cell-surface receptor, thereby increasing the specificity of binding of the adenovirus to a given cell. Alternatively, the method enables targeting of the adenovirus to a desired cell-surface receptor by the introduction of a nonnative amino acid sequence either into the penton base or the fiber knob. The nonnative amino acid sequence can be such that it enables direct or indirect binding, i.e., by means of a bispecific or multispecific binding agent, of the adenovirus to the desired cell-surface receptor.

The recombinant adenovirus preferably additionally comprises a nonnative gene that is capable of being expressed in a cell to which the recombinant adenovirus attaches or by which the recombinant adenovirus is internalized, and, optionally, a nonnative amino acid sequence in addition to or in place of a native penton base or fiber knob amino acid sequence. The nonnative amino acid sequence does not prevent assembly of the adenovirus, can be a bispecific or multispecific protein binding sequence, such as an antibody binding site, or a cellular receptor binding sequence and can be located in an exposed loop of the fiber knob or at the C-terminus of the fiber knob as a C-terminal extension. The short-shafted fiber preferably comprises a tail, a shaft comprising at least about six β repeats, preferably from about six to about twelve β repeats, and a knob. It is preferred that the shaft comprise no more than about twelve β repeats. The shaft of the short-shafted fiber and the knob can be of the same or different serotype. The shaft of the short-shafted fiber can be a portion of a shaft, such as that portion that is adjacent to the tail in a naturally occurring adenoviral fiber. The method of targeting attachment of an adenovirus to a cell for cell entry comprises contacting the cell with the above-described recombinant adenovirus such that entry of the adenovirus into the cell is effected. When the recombinant adenovirus comprises a nonnative amino acid sequence, which is a bispecific or multispecific protein binding sequence, such as an antibody binding site, initially, the recombinant adenovirus is contacted with the bispecific or multispecific binding agent, which comprises (i) a first component that selectively binds the bispecific or multispecific protein binding sequence, respectively, in the adenovirus, and (ii) a second component that selectively binds a cell surface binding site on the cell so as to form a complex of the adenovirus and the bispecific or multispecific binding agent, e.g., antibody. Then, the cell is contacted with the complex such that entry of the adenovirus into the cell is effected.

Results shown are the mean of three samples and are standardized to the control at 100. The standard deviation of the mean in all samples was 10% or lower.

Figure 7:
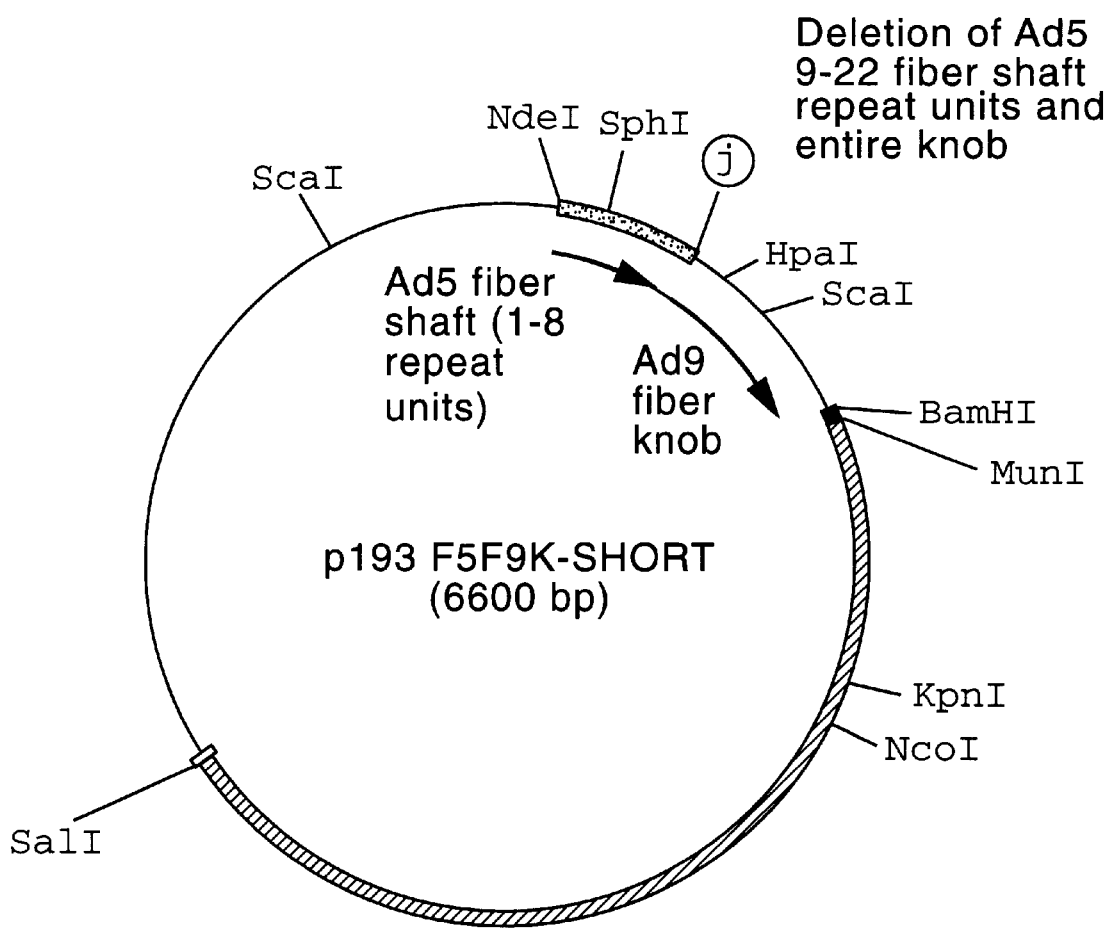

FIG. 7 is a map of the plasmid p193 F5F9K-Short.

Figure 8:
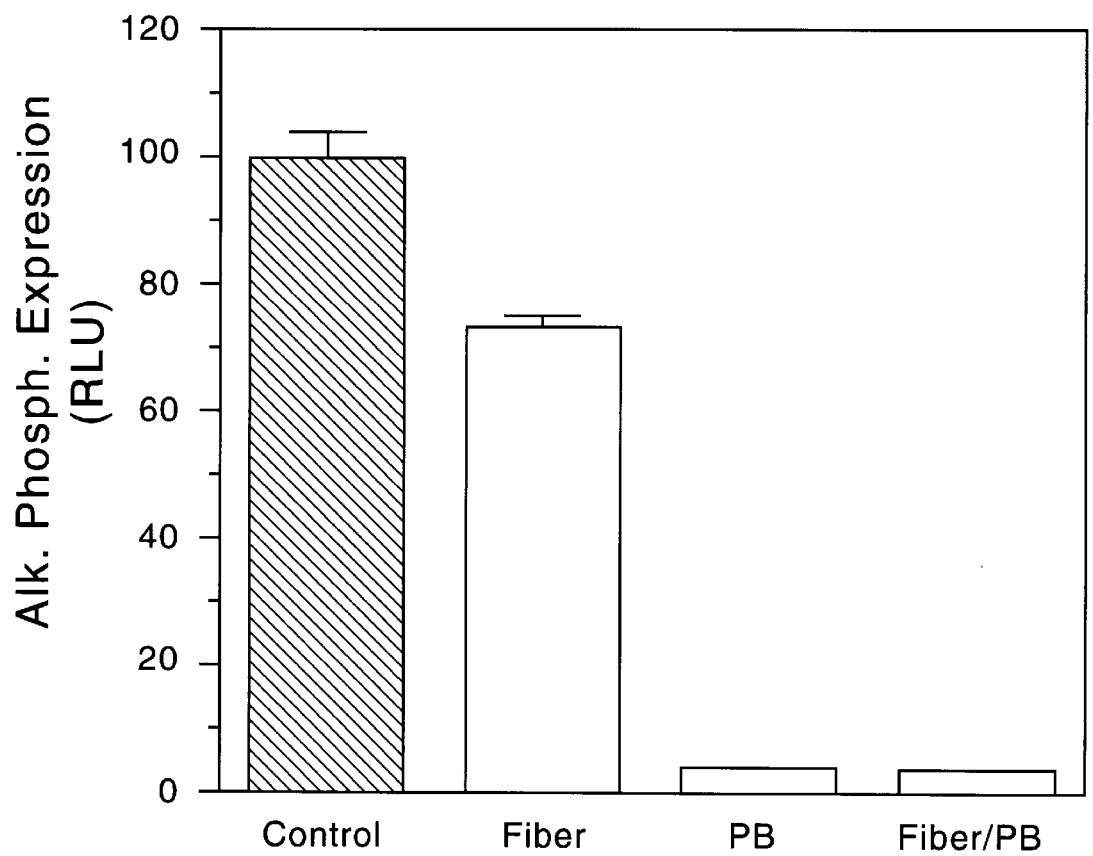

FIG. 8 is a bar graph of alkaline phosphate expression (RLU) versus control, fiber, PB, and fiber plus PB.

Figure 9:
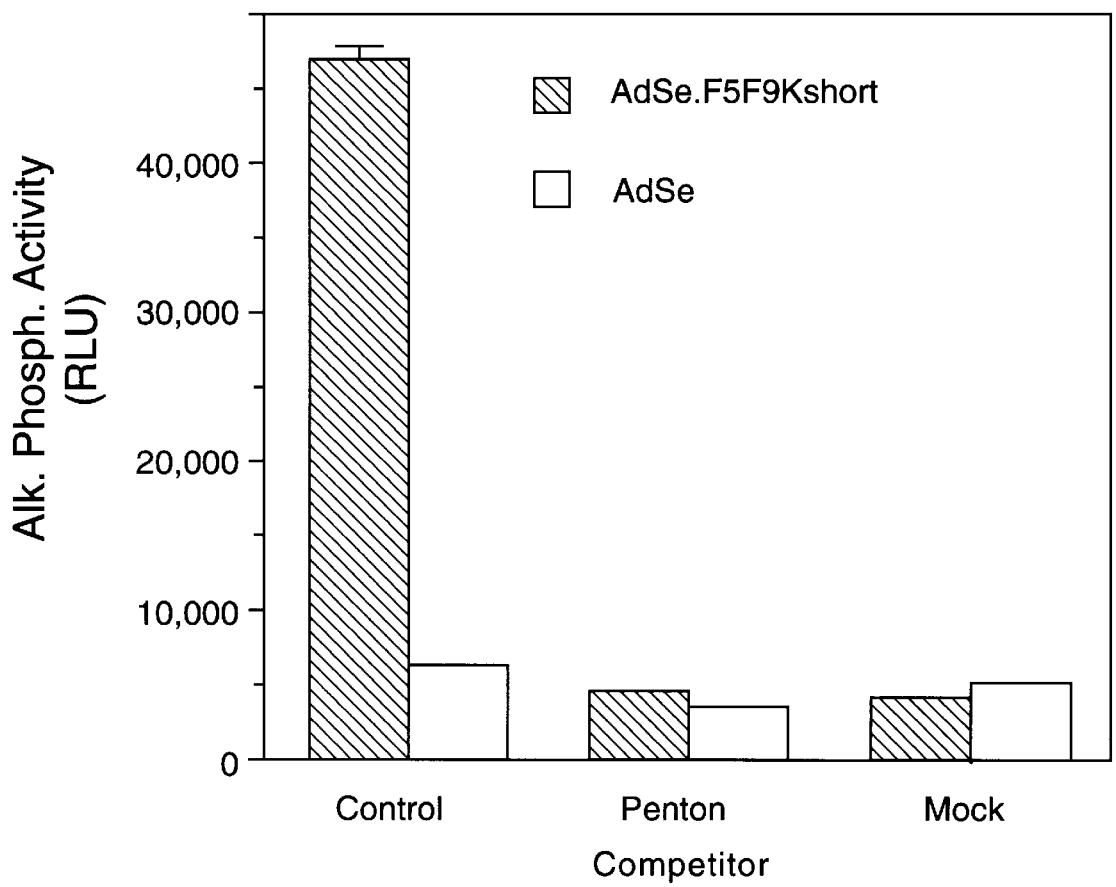

FIG. 9 is a bar graph of alkaline phosphate expression (RLU) versus control and the competitors penton and mock for AdSe.F5F9Kshort (■) and AdSe (□).

For all figures, error bars indicate standard deviation. For FIGS. 1A–4B, values are the average of triplicates.

DETAILED DESCRIPTION OF THE INVENTION

The present invention is predicated, at least in part, on the discovery that distinct subgroups of serotypes of adenovirus, which display markedly different tropisms, recognize the same cellular fiber receptor, although with markedly different binding characteristics. For example, the subgroup C viruses Ad2 and Ad5 recognize the same cellular fiber receptor as the subgroup D virus Ad9. The subgroup B virus Ad3, however, recognizes a receptor distinct from that recognized by the Ad2, Ad5 and Ad9 serotypes. Ad2 and Ad9, though, display markedly different binding characteristics. It appears that this difference in binding characteristics between Ad2 and Ad9 results from direct binding of Ad9 to cells via $\alpha_v$ integrins. Unlike Ad2, Ad9 binding to many cell lines was not abrogated by competition with the fiber 9 knob (F9K). Ad9 binding to fiber receptor-deficient cells that express $\alpha_v$ integrins, however, was blocked by a monoclonal antibody to $\alpha_v$ integrins. In contrast, Ad9 binding to $\alpha_v$ integrin-deficient cells that express fiber receptor was blocked by F9K. Similarly, transfection of an $\alpha_v\beta 5$ integrin-deficient cell line with a plasmid that expresses the $\alpha 5$ integrin subunit resulted in $\alpha_v\beta 5$ integrin expression and in Ad9 binding that was not significantly blocked by F9K but was blocked with a combination of F9K and penton base. These results indicate that the shorter length of fiber 9, which, as a member of subgroup D, is in the range of 12–13 nm, relative to fiber 2, which, along with fiber 5, are members of subgroup C and are 37 nm in length, permits fiber-independent binding of Ad9 penton base to $\alpha_v$ integrins. The shorter shaft length of the Ad9 fiber is also correlated with a reduced efficiency of fiber-mediated binding to certain cells, such as HepG2 liver cells. The difference in fiber length also explains the markedly different tissue tropisms and binding characteristics of the various adenoviral serotypes. The present invention provides the means to exploit differing fiber length to target cells with adenovirus via the addition of a nonnative binding sequence to the penton base or fiber knob, either directly or indirectly, i.e., via a bispecific or multispecific binding sequence, and/or to increase the specificity of binding of adenovirus to a given cell by decreasing the level or efficiency of fiber binding to its cellular receptor and increasing the level of penton base binding to its cellular receptor. Accordingly, the present invention provides, among other things, a short-shafted adenoviral fiber as defined herein, a recombinant adenovirus comprising such a short-shafted fiber, and a method of targeting attachment of a short-shafted recombinant adenovirus to a cell so as to effect entry of the short-shafted recombinant adenovirus into the cell.

In the context of the present invention, an "adenovirus" is any virus of the family Adenoviridae, and desirably is of the genus Mastadenovirus (e.g., mammalian adenoviruses) or Aviadenovirus (e.g., avian adenoviruses). The adenovirus is of any serotype. Adenoviral stocks that can be employed as a source of adenovirus or adenoviral coat protein, such as fiber and/or penton base, can be amplified from the adenoviral serotypes 1 through 47, which are currently available from the American Type Culture Collection (ATCC, Rockville, Md.), or from any other serotype of adenovirus available from any other source. For instance, an adenovirus can be of subgroup A (e.g., serotypes 12, 18, 31), subgroup B (e.g., serotypes 3, 7, 11, 14, 16, 21, 34, 35), subgroup C (e.g., serotypes 1, 2, 5, 6), subgroup D (e.g., serotypes 8, 9, 10, 13, 15, 17, 19, 20, 22–30, 32, 33, 36–39, 42–47), subgroup E (serotype 4), subgroup F (serotype 40, 41), or any other adenoviral serotype. Preferably, however, an adenovirus is of an Ad2, Ad5 or Ad9 serotype. Serotypes of subgroup B are least preferred. Desirably, an adenovirus comprises coat proteins (e.g., penton base, hexon, and/or fiber) of the same serotype. However, also preferably, the coat protein, such as the penton base or fiber, can be chimeric (as further defined herein) in the sense that all or a part of it is from another serotype.

Preferably, the adenovirus is replication competent. Alternatively and preferably, the adenovirus comprises a genome with at least one modification therein, optimally a modification that renders the virus replication deficient. The modification to the adenoviral genome includes, but is not limited to, deletion of a DNA segment, addition of a DNA segment, rearrangement of a DNA segment, replacement of a DNA segment, or introduction of a DNA lesion. A DNA segment can be as small as one nucleotide or as large as 36 kilobase pairs (i.e., the approximate size of the adenoviral genome) or 38 kilobase pairs, which is the maximum amount that can be packaged into an adenoviral virion (i.e., about 38 kb). Preferred modifications to the adenoviral genome include modifications affecting the fiber shaft, fiber knob, and penton base. An adenovirus also preferably can be a cointegrate, i.e., a ligation of adenoviral genomic sequences with other sequences, such as other virus, phage, or plasmid sequences.

Recombinant Adenovirus

The present invention provides a recombinant adenovirus comprising (a) a short-shafted fiber, (b) a nonnative gene that is capable of being expressed in a cell to which the recombinant adenovirus attaches or by which the recombinant adenovirus is internalized, and, optionally, a nonnative amino acid sequence in addition to or in place of a native penton base or fiber knob amino acid sequence, wherein the nonnative amino acid sequence does not prevent assembly of adenoviral particles.

By "short-shafted fiber" is meant a fiber whose shaft is shorter than that which is present in a given naturally occurring, i.e., wild-type, adenovirus. The short-shafted fiber preferably comprises a tail, a shaft and a knob. The shaft should be sufficiently shorter than the wild-type shaft for a given adenovirus such that the level or efficiency of fiber binding to its cell-surface receptor is reduced and the binding of the penton base to its cell-surface receptor is increased, thereby increasing the specificity of binding of the adenovirus to a given cell. For example, a shaft should be shorter than that which is present in Ad2 or Ad5. The shaft can be shortened by replacement of a longer fiber with a shorter fiber, which may be of a different serotype. If a shaft is shortened by replacement of the entire fiber (or the fiber shaft and knob), it is preferred that a fiber of subgroup C, such as Ad2 or Ad5, be replaced with a fiber of subgroup D, such as Ad9. In this regard, the fiber shaft and knob can be of the same serotype or the shaft can be of one serotype and the knob can be of another serotype. A fiber of subgroup B, however, is least preferred because, in spite of its short length, the fiber still binds strongly to its cell-surface receptor. A fiber of subgroup B could be used, however, if, for example, its knob were changed to the Ad9 serotype. Preferably, however, the shaft is shortened by deletion of a portion of the shaft, preferably distal to the tail. In addition, or as an alternative, the knob can be of a different serotype from that of the shaft. Accordingly, a shortened Ad2 or Ad5 fiber can be used or an Ad9 fiber can be used. Furthermore, a shortened Ad2 or Ad5 fiber shaft can be used with an Ad9 knob or an Ad9 fiber shaft can be used with an Ad2 or Ad5 knob.

Preferably, the shaft comprises at least about six β repeats, more preferably from about six to about twelve β repeats. It is preferred that the shaft comprise no more than about twelve β repeats. The shaft of the short-shafted fiber can be a portion of a shaft, such as that portion of the shaft that is adjacent to the tail in the fiber of the corresponding naturally occurring denovirus. The short-shafted fiber can be chimeric. Furthermore, the short-shafted fiber can bind an $\alpha_v$ integrin via a nonnative sequence.

By "nonnative gene" is meant any gene that is not found in the corresponding naturally occurring (i.e., wild-type) adenovirus. The nonnative gene can be any gene, and desirably is either a therapeutic gene or a reporter gene, which, preferably, is capable of being expressed in a cell entered by the adneovirus. A therapeutic gene can be one that exerts its effect at the level of RNA or protein. For instance, a protein encoded by a therapeutic gene can be employed in the treatment of an inherited disease, e.g., the use of a cDNA encoding the cystic fibrosis transmembrane conductance regulator in the treatment of cystic fibrosis. Alternatively, the protein encoded by the therapeutic gene can exert its therapeutic effect by incurring cell death. For instance, expression of the protein, itself, can lead to cell death, as with expression of diphtheria toxin A, or the expression of the protein can render cells selectively sensitive to certain drugs, e.g., expression of the *Herpes simplex* (HSV) thymidine kinase gene renders cells sensitive to antiviral compounds, such as acyclovir, gancyclovir and FIAU (1-(2-deoxy-2-fluoro-β-D-arabinofuranosil)-5-iodouracil).

Moreover, the therapeutic gene can exert its effect at the level of RNA, for instance, by encoding an antisense message or ribozyme, a protein that affects splicing or 3' processing (e.g., polyadenylation), or a protein that affects the level of expression of another gene within the cell (i.e., where gene expression is broadly considered to include all steps from initiation of transcription through production of a processed protein), perhaps, among other things, by mediating an altered rate of mRNA accumulation, an alteration of mRNA transport, and/or a change in post-transcriptional regulation. Thus, the use of the term "therapeutic gene" is intended to encompass these and any other embodiments of that which is more commonly referred to as gene therapy as known to those of skill in the art.

By "nonnative amino acid sequence" is meant any amino acid sequence that is not found in the penton base or fiber knob of a given adenovirus and which is introduced into the fiber or penton base of that adenovirus at the level of gene expression. "Nonnative amino acid sequence" includes an amino acid sequence from an adenoviral serotype other than the serotype of the adenovirus with the short-shafted fiber, in particular the serotype of the fiber shaft or knob or penton base of the adenovirus with the short-shafted fiber. Preferably, the nonnative amino acid sequence confers upon the penton base or the knob of the short-shafted fiber the ability to bind directly or indirectly, via a bispecific or multispecific binding agent, such as an antibody or fragment thereof, to a target receptor or class of target receptors, preferably a cell-specific or tissue-specific receptor. Preferably, the nonnative amino acid sequence is introduced into the penton base. However, when the nonnative amino acid sequence is introduced into the fiber knob, preferably it is introduced into an exposed loop or at the C-terminus of the fiber knob.

By "receptor" is meant a protein, carbohydrate, lipid or other molecule or moiety present on the surface of a cell, including membrane-bound and soluble proteins.

A "bispecific binding agent" according to the invention is a binding agent with specificity for at least two molecules (i.e., it can be more than two and, thus, multispecific). A bispecific binding agent can be any combination of an antibody and/or an attachment sequence, as further described herein. Such a bispecific (multispecific) binding agent preferably comprises: (i) first component that selectively binds the bispecific (multispecific) protein binding sequence in the adenovirus and (ii) a second component that selectively inds a desired cell surface binding site, such as the particular cell surface binding site present on the cell with which the adenovirus is brought into contact.

A "component" (i.e., a first or second component) is any molecule that can interact (e.g., covalently or noncovalently) with either the bispecific or multispecific protein binding site on the penton base or fiber knob or or a particular cell surface binding site. Optimally, the first and second components of the bispecific binding agent are linked to each other in some fashion, e.g., for instance, by a covalent interaction (e.g., chemical linkage and/or fusion with two or more protein domains), or by a noncovalent interaction. A component, preferably, is an antibody (e.g., a polyclonal, monoclonal, bispecific, and/or single-chain antibody) and/or an attachment sequence (e.g., such as a ligand for a cell surface binding site).

A component that is an attachment sequence preferably is a ligand (e.g., for a cell surface binding site such as a receptor). The presence of a ligand for a cell surface binding site in the bispecific (multispecific) binding agent (e.g., optimally, in the second component) provides for targeting of adenovirus to cells, which, on their surfaces, have this specific binding site for the ligand. Examples of preferred binding sites and their respective ligands or attachment sequences include, but are not limited to: CR2 receptor binding the amino acid residue attachment sequences EDPGFFNVE (i.e., Glu Asp Pro Gly Phe Phe Asn Val Glu; SEQ ID NO: 4) and EPGKQLYNVE (i.e., Glu Pro Gly Lys Gln Leu Tyr Asn Val Glu; SEQ ID NO: 5); CD4 receptor recognizing the V3 loop of HIV gp120; transferrin receptor and its ligand; low density lipoprotein receptor and its ligand; the ICAM-1 receptor on epithelial and endothelial cells in lung and its ligand; and asialoglycoproteins that recognize deglycosylated protein ligands. Moreover, additional ligands and their binding sites preferably include (but are not limited to) integrins, which recognize linear stretches of amino acids, such as the tripeptides RGD (i.e., Arg Gly Asp) and LDV (i.e., Leu Asp Val), the sequence KQAGD (i.e., Lys Gln Ala Gly Asp; SEQ ID NO: 1), and the sequence EILDV (i.e., Glu Ile Leu Asp Val; SEQ ID NO: 2), as well as polylysine (i.e., Lys Lys Lys Lys Lys; SEQ ID NO: 6, wherein the sequence can be present one to ten times) and polyarginine sequences (i.e., Arg Arg Arg Arg Arg; SEQ ID NO: 7, wherein the sequence can be present one to ten times). Inserting multiple lysines and/or arginines provides for recognition of heparin and DNA.

A component that is an antibody, e.g., directed against a particular cell surface binding site or an epitope present on a chimeric or wild-type penton base or fiber knob, can be incorporated into the bispecific binding agent, preferably in the first component. Such an antibody includes, but is not limited to, immunoglobulin molecules and immunologically active portions thereof, such as portions containing a paratope (i.e., an antigen binding site), such that the antibody comprises, for example, either intact immunoglobulin molecules or portions thereof, such as those known in the art as Fab, Fab', F(ab')$_2$ and F(v). The antibody can be, for example, a monoclonal antibody, a polyclonal antibody, a single-chain antibody (e.g., which can further comprise a ligand or attachment sequence in addition to a paratope), and a bispecific antibody (e.g., which, in and of itself, can be a bispecific molecule having one paratope directed to an epitope of a wild-type or chimeric penton base or fiber knob, and another paratope directed to an epitope of a cell surface binding site).

Preferred antibodies according to the invention are those that are directed against any cell surface binding site, particularly those previously mentioned, and those that are directed against any binding domain that constitutes an epitope present in wild-type (i.e., native) or chimeric penton base or fiber knob. Accordingly, optimally, an antibody is directed against the CR2 receptor, the CD4 receptor, the transferrin receptor, the low density lipoprotein receptor, the ICAM-1 receptor, asialoglycoproteins, and any of the integrins. Also preferably, an antibody is directed against an exposed region of a penton base or fiber knob (exposed loop or C-terminus), e.g., one that projects outward from the capsid protein and is conformationally accessible for binding to a bispecific antibody. Accordingly, further preferred antibodies of either type (i.e., those directed against either a cell surface binding site or an epitope in wild-type or chimeric penton base or fiber knob) include, but are not limited to: the L230 monoclonal antibody directed against $\alpha_v$ integrins; the M2 monoclonal antibody directed against the FLAG octapeptide DYKDDDDK (i.e., Asp Tyr Lys Asp Asp Asp Asp Lys; SEQ ID NO: 8; the L230:FLAG bispecific antibody, which incorporates the L230 and M2 monoclonal antibodies; the OKT3:FLAG bispecific antibody, which incorporates a FLAG monoclonal antibody linked to an antibody directed against the CD3 T-cell receptor; the ICAM:FLAG bispecific antibody, which incorporates a FLAG monoclonal antibody linked to an antibody directed against the ICAM-1 receptor; the P1F6 antibody directed against the integrin $\alpha_v\beta_5$; the 1B1.3.2 monoclonal antibody directed against the $\alpha v$ subunit of $\alpha_v$ integrins; and the 12CA5 monoclonal antibody directed against the hemagluttinin peptide.

The antibody can be produced by any suitable technique, e.g., conventional techniques for preparing monoclonal, polyclonal, single-chain, and bispecific antibodies, as well as more current recombinant DNA techniques that are familiar to those skilled in the art. For instance, antibodies directed against adenovirus in particular can be made as described, for example, in U.S. Pat. No. 4,487,829. Chimeric molecules having a ligand component linked to an immunoglobulin constant region, and other immunoconjugates, such as bispecific antibodies, can be made as described, for instance, in U.S. Pat. Nos. 4,816,567, 5,349,053, 5,332,567, and 5,443,953, and PCT international patent application nos. WO 90/14424, WO 91/05805, WO 91/05871, WO 92/02553, and WO 95/16037; Cook et al., *J. Immunol. Methods*, 171, 227–237 (1994); and Spooner et al., *Human Pathol.*, 25, 606–614 (1994). In particular, bispecific antibodies can be made by a variety of means, e.g., chemical techniques (see, e.g., Kranz et al., PNAS (USA), 78, 5807 (1981)), for instance, disulfide cleavage reformation of whole IgG or, preferably, F(ab')$_2$ fragments; fusions of more than one clone to form polyomas that produce immunoglobulins having more than one specificity (see, e.g., U.S. Pat. No. 4,474,893; Segal et al., *In Current Protocols in Immunology*, Coligan et al. (eds.), vol. 1, 2.13.1–2.13.16 (John Wiley & Sons, Inc. (1995)); or by genetic engineering (see, e.g., U.S. Pat. No. 4,816,567 and PCT international patent application no. WO 90/14424).

A component, such as an antibody and/or an attachment sequence comprising a bispecific molecule, "selectively binds" a binding domain of an adenoviral penton base or fiber knob and/or a cell surface binding site when it interacts with that binding domain and/or cell surface binding site with a greater affinity, or is more specific for or has greater specificity for that binding domain and/or cell surface binding site, as compared with other binding domains and/or cell surface binding sites. The terms "has specificity for" and "is specific for" refer to the degree of selectivity shown by a peptide or protein with respect to the number and types of reactants with which the protein interacts and the rates and extent of these reactions, the degree of selectivity shown by an antibody with respect to the number and types of antigens with which the antibody combines and the rates and the extent of these reactions, or refers to the type and the degree of permeability to substances transported across the membrane by a cell surface binding protein. The term "selectively binds" in the present context means binding sufficient to be useful in the method of the invention. As is known in the art, useful selective binding, for instance, to a receptor, depends on both the binding affinity and the concentration of ligand achievable in the vicinity of the receptor. Thus, binding affinities lower than that found for any naturally occurring competing ligands are useful, so long as the cell or tissue to be treated can tolerate concentrations of added ligand sufficient to compete, for instance, for binding to a cell surface receptor.

A "bispecific or multispecific protein binding sequence" is a region on either the penton base or the fiber knob (in an exposed loop or C-terminus) with which a component interacts. This interaction can be either a covalent or non-covalent interaction. A bispecific or multispecific protein binding sequence can comprise an epitope (i.e., an antigenic determinant or the portion of an antigen that combines with an antibody in an antigen-antibody reaction). A bispecific or multispecific protein binding sequence also preferably is a peptide sequence or protein domain that is capable of recognizing a cell surface binding site. It also, preferably, is a "coupler" protein sequence that is used to couple other proteins to the fiber knob or penton base. An example of this is a sequence, such as those described in the art, that mediates biotin-avidin (streptavidin) binding (e.g., as described by Saggio et al., *Biochem. J.*, 293, 613–616 (1993); Alon, *Eur. J. Immunol.*, 23, 893–898 (1993); Miller et al., *Biochem. J.*, 278, 573–585 (1991)) and serve as attachment sites for avidin and biotin conjugated proteins.

Accordingly, preferably, a bispecific or multispecific protein binding domain comprises any of the aforementioned attachment sequences, e.g., EDPGFFNVE (i.e., Glu Asp Pro Gly Phe Phe Asn Val Glu; SEQ ID NO: 4) and EPGKQ-LYNVE (i.e., Glu Pro Gly Lys Gln Leu Tyr Asn Val Glu; SEQ ID NO: 5) recognized by the CR2 receptor; the V3 loop of HIV gp120 recognized by the CD4 receptor; the ligand transferrin recognized by the transferrin receptor; the ligand for the low density lipoprotein receptor; the ligand for the ICAM-1 receptor on epithelial and endothelial cells in lung; deglycosylated protein ligands recognized by asialoglycoprotein; linear stretches of amino acids recognized by integrins, such as the tripeptides RGD (i.e., Arg Gly Asp) and LDV (i.e., Leu Asp Val), the sequence KQAGD (i.e., Lys Gln Ala Gly Asp; SEQ ID NO: 1), and the sequence EILDV (i.e., Glu Ile Leu Asp Val; SEQ ID NO: 2), as well as polylysine (i.e., Lys Lys Lys Lys Lys; SEQ ID NO: 6, wherein the sequence can be present one to ten times) and polyarginine (i.e., Arg Arg Arg Arg Arg; SEQ ID NO: 7, wherein the sequence can be present one to ten times) sequences, which provide for recognition of heparin and DNA.

Also, preferably, a bispecific or multispecific protein binding domain comprises an epitope for: the M2 monoclonal antibody directed against the FLAG octapeptide DYKDDDDK (i.e., Asp Tyr Lys Asp Asp Asp Asp Lys; SEQ ID NO: 8); the L230:FLAG bispecific antibody, which incorporates the L230 and M2 monoclonal antibodies; the OKT3:FLAG bispecific antibody, which incorporates a FLAG monoclonal antibody linked to an antibody directed against the CD3 T-cell receptor; the ICAM:FLAG bispecific antibody, which incorporates a FLAG monoclonal antibody linked to an antibody directed against the ICAM-1 receptor; or the 12CA5 monoclonal antibody directed against the hemagluttinin peptide. The binding domain an comprise a portion of the wild-type sequence in part, and a portion of the non-wild-type sequence in part. Similarly, the sequences (either native and/or nonnative) that comprise the binding sequence need not necessarily be contiguous in the chain of amino acids that comprise the protein. In other words, the binding sequence can be generated by the particular conformation of the protein, e.g., through folding of the protein in such a way as to bring contiguous and/or noncontiguous sequences into mutual proximity.

Vectors

The recombinant adenovirus comprising a short-shafted fiber and the recombinant adenovirus that additionally comprises a nonnative gene or genes capable of being expressed in a particular cell can be generated by use of a viral transfer vector, preferably an adenoviral transfer vector, in accordance with the present invention. The viral transfer vector, preferably an adenoviral transfer vector, comprises a gene sequence encoding a short-shafted fiber as defined herein. Preferably, the short-shafted fiber gene sequence comprises a gene for a shorter fiber (as compared to wild-type) and, more preferably, a portion of a fiber gene. Preferably, the fiber gene sequence comprises a portion of a fiber gene encoding at least about six β repeats, preferably from about six to about 12 β repeats. It is preferred that the fiber gene sequence comprise no more than about twelve β repeats. Preferably, the portion of the fiber gene encoding at least about six β repeats is that portion of the fiber gene encoding those repeats adjacent to the tail in the fiber of a naturally occurring, i.e., wild-type, adenovirus.

Accordingly, the invention also provides a vector comprising a gene sequence encoding a short-shafted fiber as defined herein. A "vector" is a vehicle for gene transfer as that term is understood by those of skill in the art. The vectors according to the invention include, but are not limited to, plasmids, phages, and viruses. Preferably, a vector according to the invention is an adenoviral vector. An example of a preferred vector is AdSe.F5F9Kshort. The vectors according to the invention are not limited to those that can be employed in the method of the invention, but also include intermediary-type vectors (e.g., "transfer vectors") that can be employed in the construction of gene transfer vectors. Examples of such transfer vectors are provided in the Examples set forth below. Preferably, the vector further comprises a nonnative gene as described above.

In terms of an adenoviral vector (particularly a replication-deficient adenoviral vector), such a vector can comprise either complete capsids (i.e., including a viral genome, such as an adenoviral genome) or empty capsids (i.e., in which a viral genome is lacking, or is degraded, e.g., by physical or chemical means). Preferably, the viral vector comprises complete capsids, i.e., as a means of carrying one or more nonnative genes. Alternatively, preferably, a nonnative gene, as defined above, is carried into a cell on the outside of the adenoviral capsid. Along the same lines, since methods are available for transferring viruses, plasmids, and phages in the form of their nucleic acid sequences (i.e., RNA or DNA), a vector similarly can comprise RNA or DNA, in the absence of any associated protein such as capsid protein, and in the absence of any envelope lipid. Similarly, since liposomes effect cell entry by fusing with cell membranes, a vector can comprise liposomes, with constitutive nucleic acids encoding the coat protein. Such liposomes are commercially available, for instance, from Life Technologies, Bethesda, Md., and can be used according to the recommendation of the manufacturer. Moreover, a liposome can be used to effect gene delivery. The soluble chimeric coat protein (as produced using methods described herein) can be added to the liposomes either after the liposomes are prepared according to the manufacturer's instructions, or during the preparation of the liposomes.

A vector according to the invention can comprise additional sequences and mutations, e.g., within the adenoviral short-shafted fiber, such as the knob, and/or penton base protein and/or nonnative gene sequences. In particular, a vector according to the invention preferably further comprises a nucleic acid comprising a nonnative gene, as defined above, which can comprise a wholly or partially synthetically made coding or other genic sequence or a genomic or complementary DNA (cDNA) sequence and can be provided in the form of either DNA or RNA.

A recombinant short-shafted adenoviral fiber gene sequence can be moved to or from an adenoviral vector from or into baculovirus or a suitable prokaryotic or eukaryotic expression vector for expression of mRNA and production of protein, and for evaluation of receptor or protein specificity and avidity, trimerization potential, penton base binding, and other biochemical characteristics. In particular, the method of protein production in baculovirus as described in Wickham et al. (1995), supra, can be employed.

Accordingly, the present invention also provides recombinant baculoviral and prokaryotic and eukaryotic plasmids and expression vectors comprising a gene sequence encoding a short-shafted fiber as defined herein, which also are "transfer vectors" as defined herein. The short-shafted fiber gene sequence can include a nonnative sequence in addition to or in place of a native amino acid sequence, which enables the resultant chimeric short-shafted fiber to bind to a desired cell-surface receptor directly or indirectly, i.e., via a bispecific or multispecific binding agent.

By moving the chimeric gene from an adenoviral vector, PCR product or the cloning vector to baculovirus or a prokaryotic or eukaryotic expression vector, high protein expression is achievable (approximately 5–50% of the total protein being the chimeric fiber).

A vector according to the invention further can comprise, either within, in place of, or outside of the coding sequence of the gene sequence encoding a short-shafted fiber as described herein, additional sequences that impact upon the ability of a short-shafted fiber protein to trimerize, for example. A sequence that impacts upon the ability to trimerize is a sequence that enables trimerization of a chimeric short-shafted fiber in the context of the present invention.

In terms of the production of vectors according to the invention (including recombinant adenoviral vectors and transfer vectors), transfer vectors can be constructed using standard molecular and genetic techniques such as are known to those skilled in the art.

Vectors comprising virions or virus particles (e.g., recombinant adenoviral vectors) can be produced using viral vectors in the appropriate cell lines. Similarly, the fiber chimera-containing particles can be produced in standard cell lines, e.g., those currently used for adenoviral vectors. These resultant particles then can be targeted to specific cells via the penton base, which can comprise a nonnative amino acid sequence as defined herein, or via the fiber, the knob of which can comprise a nonnative amino acid sequence as defined herein. The targeting can be direct or indirect, e.g., via a bispecific or multispecific binding agent, e.g., an antibody or fragment thereof.

Short-Shafted Adenoviral Fiber

Accordingly, the present invention also provides a short-shafted adenoviral fiber. Desirably, the short-shafted adenoviral fiber is derived from a wild-type adenoviral fiber (or its encoding nucleic acid sequence), such as by replacement of a longer fiber or a longer shaft and knob with a shorter fiber or a shorter shaft and knob, or, preferably, by deletion of a portion of the shaft of a wild-type adenoviral fiber, preferably distal to the tail. In addition, or as an alternative, the knob can be of the same or a different serotype from that of the shaft. Although any serotype of adenovirus can be used as a source of fiber (i.e., either as a source of DNA for generating the protein by recombinant means, or as a source of the protein, itself), a serotype from subgroup C, such as Ad2 or Ad5, or D, such as Ad9, is preferred, with a serotype from subgroup B being least preferred. The ordinary skilled artisan is well versed in the means of protein production.

Preferably, the short-shafted fiber is shorter than that of Ad2 or Ad5 and comprises at least about six β repeats, more preferably from about six to about twelve β repeats, and even more preferably comprises at least about six β repeats from the region of the fiber shaft adjacent the tail in a naturally occurring adenovirus. It is preferred, however, that the shaft comprise no more than about twelve β repeats. The short-shafted fiber may additionally comprise an addition to the wild-type protein or replacement in the protein of an amino acid sequence. Such an addition or replacement is preferably made such that the chimeric short-shafted fiber comprises a bispecific or multispecific protein binding sequence (i.e., an attachment sequence or an epitope for an antibody, as previously described) or a cellular receptor binding sequence, such as a sequence for binding to an integrin, in the fiber knob.

Desirably, the bispecific or multispecific protein binding sequence (as defined above) in a chimeric short-shafted fiber protein constitutes an addition to the wild-type protein or replacement in the protein of an amino acid sequence of between about one and about two hundred fifty amino acids, more preferably between about one and about one hundred amino acids, and, optimally, between about one and about fifty amino acids in the fiber knob. Alternatively, the adenoviral penton base comprises a bispecific or multispecific protein binding sequence as defined above that effects binding to a particular molecule that the corresponding, naturally occurring, i.e., wild-type, adenoviral penton base protein does not bind. Alternatively, preferably, the chimeric adenoviral penton base or fiber knob comprises a nonnative amino acid sequence that binds a molecule, such as a cellular receptor, not bound by a naturally occurring, i.e., wild-type, penton base or fiber knob, respectively.

Accordingly, the proteins (and peptides) according to the invention can be prepared by any of a number of conventional techniques. For instance, in the case of recombinant peptides, a DNA fragment encoding a desired peptide can be subcloned into an appropriate vector using well known molecular genetic techniques (see, e.g., Maniatis et al., *Molecular Cloning: A Laboratory Manual*, 2nd ed. (Cold Spring Harbor Laboratory, 1989)). The fragment can be transcribed and the peptide subsequently translated in vitro. Commercially available kits also can be employed (e.g., such as manufactured by Clontech, Palo Alto, Calif.; Amersham Life Sciences, Inc., Arlington Heights, Ill.; InVitrogen, San Diego, Calif., and the like). The polymerase chain reaction optionally can be employed in manipulation of nucleic acids.

Alterations of the native amino acid sequence to produce variant peptides can be done by a variety of means known to those skilled in the art. A variant peptide is a peptide that is substantially homologous to another indicated peptide, but which has an amino acid sequence that differs from that peptide. The degree of homology (i.e., percent identity) can be determined, for instance, by comparing sequence information using a computer program optimized for such comparison (e.g., using the GAP computer program, version 6.0 or a higher version, described by Devereux et al. (*Nucleic Acids Res.*, 12, 387 (1984)), and freely available from the University of Wisconsin Genetics Computer Group (UWGCG)).

The activity of the variant proteins and/or peptides can be assessed, for instance, by examining transduction ability or cell binding ability imparted by a chimeric penton base or chimeric knob, in combination with a short-shafted fiber protein, or using other methods known to those skilled in the art.

In terms of amino acid residues that are not identical between the variant protein (peptide) and the reference protein (peptide), the variant proteins (peptides) preferably comprise conservative amino acid substitutions, i.e., such that a given amino acid is substituted by another amino acid of similar size, charge density, hydrophobicity/hydrophilicity, and/or configuration (e.g., Val for Phe). The variant site-specific mutations can be introduced by ligating into an expression vector a synthesized oligonucleotide comprising the modified site. Alternately, oligonucleotide-directed site-specific mutagenesis procedures can be used, such as those disclosed in Walder et al., *Gene*, 42, 133 (1986); Bauer et al., *Gene*, 37, 73 (1985); Craik, *Biotechniques*, 12–19 (January 1995); and U.S. Pat. Nos. 4,518,584 and 4,737,462.

Any appropriate expression vector (e.g., as described in Pouwels et al., *Cloning Vectors: A Laboratory Manual* (Elsevier, N.Y.: 1985)) and corresponding suitable host can be employed for production of recombinant peptides. Expression hosts include, but are not limited to, bacterial species within the genera Escherichia, Bacillus, Pseudomonas, Salmonella, mammalian or insect host cell systems, including baculoviral systems (e.g., as described by Luckow et al., *Bio/Technology*, 6, 47 (1988)), and established cell lines, such as the COS-7, C127, 3T3, CHO, HeLa, BHK cell line, and the like. An especially preferred expression system for preparing chimeric proteins (peptides) according to the invention is the baculoviral expression system (e.g., as described in Wickham et al. (1995), supra), wherein *Trichoplusia ni*, Tn 5B1-4 insect cells, or other appropriate insect cells, are used to produce high levels of recombinant proteins. The ordinary skilled artisan is, of course, aware that the choice of expression host has ramifications for the type of peptide produced. For instance the glycosylation of peptides produced in yeast or mammalian cells (e.g., COS-7 cells) will differ from that of peptides produced in bacterial cells, such as *Escherichia coli.*

Alternatively, the peptides of the invention (including the variant peptides) can be synthesized using standard peptide synthesizing techniques well known to those of skill in the art (e.g., as summarized in Bodanszky, *Principles of Peptide Synthesis*, (Springer-Verlag, Heidelberg: 1984)). In particular, the peptides can be synthesized using the procedure of solid-phase synthesis (see, e.g., Merrifield, *J. Am. Chem. Soc.*, 85, 2149–54 (1963); Barany et al., *Int. J. Peptide Protein Res.*, 30, 705–739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the peptide from the resin can be accomplished by, for example, acid treatment at reduced temperature. The peptide-containing mixture can then be extracted, for instance, with dimethyl ether, to remove non-peptide organic compounds, and the synthesized peptides can be extracted from the resin powder (e.g., with about 25% w/v acetic acid). Following the synthesis of the peptide, further purification (e.g., using high performance liquid chromatography (HPLC)) optionally can be done in order to eliminate any incomplete peptides or free amino acids. Amino acid and/or HPLC analysis can be performed on the synthesized peptides to validate the identity of the peptide.

If desired, either the peptides or the proteins of the invention (including the variant peptides or proteins) can be modified, for instance, by glycosylation, amidation, carboxylation, or phosphorylation, or by the creation of acid addition salts, amides, esters, in particular C-terminal esters, and N-acyl derivatives of the peptides of the invention. The peptides also can be modified to create peptide derivatives by forming covalent or noncovalent complexes with other moieties. Covalently-bound complexes can be prepared by linking the chemical moieties to functional groups on the side chains of amino acids comprising the peptides, or at the N- or C-terminus. Such modifications can be particularly useful, for instance, in constructing bispecific molecules having a ligand to a cell surface receptor attached to an antibody. Further modifications will be apparent to those of ordinary skill in the art.

Various characteristic parameters of the short-shafted fiber protein of interest can be assessed. Specificity and affinity of the receptor or other protein/short-shafted fiber interaction can be assessed by Scatchard analysis as shown previously by Wickham et al. (1993), supra, for wild-type penton base protein. Receptor specificity can be further assessed by using antibodies and peptides specific for the targeted receptor to block short-shafted fiber binding to cells, using conventional methods. Short-shafted fiber binding to penton base protein can be assessed by its ability to precipitate radiolabeled penton base protein when coupled to protein A-coated beads via an antibody to the short-shafted fiber protein.

Viral attachment, entry and gene expression can be evaluated initially by using the adenoviral vector containing the insert of interest to generate a recombinant virus expressing the short-shafted fiber protein and a marker gene, such as β-galactosidase. β-galactosidase expression in cells infected with adenovirus containing the β-galactosidase gene (Ad-LacZ) can be detected as early as two hours after adding Ad-Gluc to cells. This procedure provides a quick and efficient analysis of cell entry of the recombinant virus and gene expression, and is implemented readily by an artisan of ordinary skill using conventional techniques.

Method of Targeting Attachment of an Adenovirus to a Cell

The present invention also provides a method of targeting attachment of an adenovirus to a cell for cell entry. The method comprises contacting the cell with a recombinant adenovirus described above such that entry of the adenovirus into the cell is effected.

By "targeting" is meant preferential introduction into a particular cell rather than into another cell. According to the invention, a cell can be any cell, and, preferably, is a eukaryotic cell. Preferably, the eukaryotic cell is of a multicellular species (e.g., as opposed to a unicellular yeast cell), and, even more preferably, is a mammalian, e.g., human, cell. Desirably, such a eukaryotic cell is one in which an adenovirus can exist for a period of time (i.e., typically from anywhere up to, and potentially even after, about two months) after entry into the cell. Optimally, nascent RNA is transcribed from the adenoviral genome, which preferably includes a nonnative gene, carried into the cell by the adenovirus, as further described herein.

A cell can be present as a single entity, or can be part of a larger collection of cells. Such a "larger collection of cells" can comprise, for instance, a cell culture (either mixed or pure), a tissue (e.g., epithelial or other tissue), an organ (e.g., heart, lung, liver, gallbladder, urinary bladder, eye, and other organs), an organ system (e.g., circulatory system, respiratory system, gastrointestinal system, urinary system, nervous system, integumentary system or other organ system), or an organism (e.g., a bird, mammal, or the like). Preferably, the organs/tissues/cells being targeted are of the circulatory system (e.g., including, but not limited to heart, blood vessels, and blood), respiratory system (e.g., nose, pharynx, larynx, trachea, bronchi, bronchioles, lungs, and the like), gastrointestinal system (e.g., including mouth, pharynx, esophagus, stomach, intestines, salivary glands, pancreas, liver, gallbladder, and others), urinary system (e.g., such as kidneys, ureters, urinary bladder, urethra, and the like), nervous system (e.g., including, but not limited to, brain and spinal cord, and special sense organs, such as the eye) and integumentary system (e.g., skin). Even more preferably, the cells being targeted are selected from the group consisting of heart, blood vessel, lung, liver, gallbladder, urinary bladder, and eye cells.

In particular, a cell to which a recombinant adenovirus is targeted differs from another cell, which is not targeted, in that the cell so being targeted comprises a particular cell surface binding site. By "particular cell surface binding site" is meant any site (i.e., molecule or combination of molecules) present on the surface of a cell with which the adenovirus can interact to attach to the cell and, thereby, promote cell entry. A particular cell surface binding site, therefore, encompasses a cell surface receptor and, preferably, is a protein (including a modified protein), a carbohydrate, a glycoprotein, a proteoglycan, a lipid, a mucin molecule or mucoprotein, and the like. Examples of potential cell surface binding sites include, but are not limited to: heparin and chondroitin sulfate moieties found on glycosaminoglycans; sialic acid moieties found on mucins, glycoproteins, and gangliosides; major histocompatability complex I (MHC I) glycoproteins; common carbohydrate molecules found in membrane glycoproteins, including mannose, N-acetyl-galactosamine, N-acetyl-glucosamine, fucose, and galactose; glycoproteins such as ICAM-1, VCAM, E-selectin, P-selectin, L-selectin, and integrin molecules; and tumor-specific antigens present on cancerous cells, such as, for instance, MUC-1 tumor-specific epitopes.

However, the present method of targeting an adenovirus to a cell is not limited to any specific mechanism of cellular interaction (i.e., interaction with a given cell surface binding site), and is not to be so construed.

When the method of targeting attachment of one of the above-described recombinant adenoviruses involves the use of a bi-specific or multi-specific binding agent, the method comprises (a) contacting the adenovirus with a bispecific or multispecific binding agent comprising (i) a first component that selectively binds the bispecific or multispecific protein binding sequence, respectively, in the adenovirus (e.g., antibody binding site), and (ii) a second component that selectively binds a cell surface binding site on the cell so as to form a complex of the adenovirus and the bispecific or multispecific binding agent, such as an antibody; and (b) contacting the cell with the complex of (a) such that entry of the adenovirus into the cell is effected.

In order to optimize the ability of the adenovirus to enter the cell by the method of the invention, the method is preferably carried out in the absence of neutralizing antibodies directed against the particular adenovirus being introduced intracellularly. In the absence of such antibodies, there is no possibility of the adenovirus being bound by the antibody and, thus, impeded from binding and/or entering the cell. It is well within the ordinary skill of one in the art to test for the presence of such neutralizing antibodies. In the event the presence of such neutralizing antibodies are an obstacle to the intracellular delivery of an adenovirus, another adenoviral vector, e.g., another serotype adenoviral vector (Crompton et al., *J. Gen. Virol.*, 75, 33–139 (1994)), or another adenoviral vector, which loacks the epitope against which the antibody is directed, can be employed.

A "complex" of the adenovirus and the bispecific (multispecific) molecule is any interaction, e.g., covalent or noncovalent, between the adenovirus and the bispecific (multispecific) molecule, and, preferably, is a noncovalent interaction. Such "contacting" can be done by any means known to those skilled in the art, and described herein, by which the apparent touching or mutual tangency of the adenovirus and bispecific (multispecific) molecule or of the cell and the complex of the adenovirus and the bispecific (multispecific) molecule can be effected. For instance, contacting of the adenovirus and the bispecific (multispecific) molecule can be done by mixing these elements in a small volume of the same solution. Optionally, the elements further can be covalently joined, e.g., by chemical means known to those skilled in the art, or other means, or, preferably, can be linked by means of noncovalent interactions (e.g., ionic bonds, hydrogen bonds, Van der Waals forces, and/or nonpolar interactions). In comparison, the cell and the complex need not necessarily be brought into contact in a small volume, as, for instance, in cases where the complex is administered to a host (e.g., a human), and the complex travels by the bloodstream to the cell in which it selectively binds and enters. The contacting of the adenovirus with a bispecific (multispecific) molecule preferably is done before the cell is contacted with the complex of the adenovirus and the bispecific (multispecific) molecule. By "before" is meant any amount of time prior to contacting the cell sufficient to ensure that a complex of the adenovirus and the bispecific molecule is formed prior to the complex contacting the cell, e.g., a period of time that ranges from about five minutes to about five years (or, to about as long as the maximum length of time a complex of an adenovirus and a bispecific molecule can be stably maintained in a useable form, for instance, lyophilized, or in the presence of cryoprotective agents at −80° C.).

There are multiple preferred embodiments of the method of the present invention. For instance, the method preferably is carried out wherein the adenovirus comprises a nonnative gene, as described herein. Also, the method preferably is carried out wherein the cell that comprises a particular cell surface binding site is one that the corresponding wild-type adenovirus typically does not bind (i.e., transduce or infect), or binds with an apparent low efficiency. However, the method also preferably can be carried out to introduce adenovirus into any cell, even a cell that wild-type adenovirus binds and enters with relatively high efficiency (e.g., epithelial cells).

The method can be carried out such that the bispecific molecule is a bispecific antibody comprising (a) a first antibody that selectively binds a bispecific protein binding sequence in the fiber knob or the penton base, and (b) a second antibody that selectively binds the cell surface binding site present on the surface of the cell with which the adenovirus is being brought into contact so as to effect cell entry of the adenovirus. This method optionally is carried out using either an adenovirus that comprises a wild-type or chimeric adenoviral penton base, as further described herein. The chimeric adenoviral penton base preferably comprises a nonnative amino acid sequence that is a binding domain that effects binding to a particular molecule, which wild-type adenoviral penton base does not bind. The binding domain of the chimeric adenoviral penton base (like the binding domain of the wild-type adenoviral penton base) preferably comprises an epitope for the first antibody. Preferably, the epitope of the chimeric adenoviral penton base protein comprises a sequence selected from the group consisting of SEQ ID NO: 8 (i.e., DYKDDDDK, or Asp Tyr Lys Asp Asp Asp Asp Lys), SEQ ID NO: 9 (i.e., TSEAAAHAIRGDTY-ADYKDDDDKGSS or Thr Ser Glu Ala Ala Ala His Ala Ile Arg Gly Asp Thr Tyr Ala Asp Tyr Lys Asp Asp Asp Asp Lys Gly Ser Ser), SEQ ID NO: 10 (i.e., TSEAAAHAIRGDTY-PYDVPDYAGSS or Thr Ser Glu Ala Ala Ala His Ala Ile Arg Gly Asp Thr Tyr Pro Tyr Asp Val Pro Asp Tyr Ala Gly Ser Ser), and SEQ ID NO: 11 (i.e., YPYDVPDYA or Tyr Pro Tyr Asp Val Pro Asp Tyr Ala) or derivations of these sequences (i.e., comprising deletions and/or mutations) that are recognized by either the M2 or 12CA5 monoclonal antibodies, or other antibodies directed against either the FLAG or hemagglutinin peptides (U.S. patent application Ser. No. 08/634, 060).

The method of the present invention also preferably is carried out wherein it further comprises abrogating (i.e., preventing) the binding of the fiber of the adenovirus being targeted for attachment to a cell. In particular, preferably the binding of the adenoviral fiber to any cell surface binding site by which adenovirus can effect cell entry is abrogated. In this preferred embodiment, any interaction of the fiber with its cell surface receptor is eliminated, thus precluding any of these interactions from interfering with the ability of the penton base to target cell binding/cell entry to a particular cell surface receptor. In any embodiment according to the invention, however, desirably it is the penton base of adenovirus that commands cell binding/cell entry.

This method preferably is carried out wherein the adenovirus comprises either a chimeric or wild-type penton base, as described above, and as further described herein. For instance, desirably, binding is abrogated by contacting the adenovirus with an antibody that selectively binds an epitope of the wild-type adenoviral fiber. Preferably, this antibody (or other agent) binds in such a manner as to prevent interaction of the adenoviral fiber with its receptor. Even more preferably, the antibody is a function-blocking antibody.

Alternatively, preferably the adenovirus employed in the method (comprising either a chimeric or wild-type penton base) further comprises a chimeric adenoviral fiber. Optionally, the binding of the chimeric adenoviral fiber is abrogated by contacting the adenovirus with an antibody or other agent that selectively binds an epitope of the chimeric adenoviral fiber. Desirably, this antibody (or other agent) binds in such a fashion as to prevent interaction of the adenoviral fiber with its receptor.

The short-shafted adenovirus also desirably can comprise a chimeric adenoviral fiber knob that is characterized by being naturally unable to bind to a cell to which the corresponding wild-type adenoviral fiber knob can bind. For instance, the adenoviral fiber knob can comprise a nonnative amino acid sequence that is a binding domain for a different cellular receptor and/or the fiber knob can be of a serotype that is different from the serotype of the shaft. The switching of fiber proteins to form a short-shafted adenovirus further is advantageous in that the shorter length of the chimeric fiber protein employed in the method preferably will allow bispecific antibodies complexed to the penton base to inhibit sterically the interaction of the chimeric fiber (e.g., the Ad9 fiber) with the adenoviral fiber receptor.

In still other preferred embodiments of the present invention, the method of introducing an adenovirus into a cell that comprises a particular cell surface binding site is preferably carried out using the recombinant adenoviral vectors of the invention as described herein.

Illustrative Uses

A vector of the present invention has utility in vitro. Such a vector can be used as a research tool in the study of adenoviral attachment and infection of cells and in a method of assaying binding site-ligand interaction. Similarly, an adenoviral vector, in particular an adenoviral vector comprising a short-shafted adenoviral fiber gene, can be employed in vivo.

In particular, recombinant adenoviruses of the present invention can be used to treat any one of a number of diseases by delivering to targeted cells corrective DNA, i.e., DNA encoding a function that is either absent or impaired, or a discrete killing agent, e.g., DNA encoding a cytotoxin that, for example, is active only intracellularly, or DNA encoding ribozymes or antisense molecules, for example. Accordingly, use of the term "nonnative adenoviral gene" (e.g., as encoding a "therapeutic agent") is intended to encompass these and other embodiments of that which is more commonly referred to as gene therapy as known to those of skill in the art. Diseases that are candidates for such treatment include, for example, cancer, e.g., melanoma or glioma, cystic fibrosis, genetic disorders, and pathogenic infections, including HIV infection.

For instance, a recombinant adenovirus having a short-shafted fiber recognized by $\alpha_v\beta_3$ receptors can be used to treat melanoma or glioma, and a recombinant adenovirus recognized by $\alpha_3\beta_1$ receptors and expressing the cystic fibrosis transmembrane regulator (CFTR) gene can be used to treat cystic fibrosis by delivery to the epithelial cells of the lungs. Furthermore, various blood-related diseases can be treated by using a recombinant adenovirus recognized by $\alpha_m\beta_2$ receptors to target neutrophils and macrophages, a recombinant adenovirus recognized by $\alpha_4\beta_1$ receptors to target lymphocytes, a recombinant adenovirus recognized by $\alpha_{IIb}\beta_3$ receptors to target platelets and megakaryocytes, and a recombinant adenovirus recognized by $\alpha_v\beta_3$ integrins to target endothelial cells undergoing angiogenesis.

The $\alpha_v$ integrins are tissue-specific receptors useful for targeted gene therapy. $\alpha_v$ integrin expression is activated in a majority of melanomas (Albelda et al., Cancer Res., 50, 6757–6764 (1990)) and gliomablastomas (Gladson et al., J. Clin. Invest., 88, 1924 (1991)). Targeting therapeutic adenovirus to the $\alpha_v$ integrins on these cells allows delivery of a toxic gene, for example, while avoiding gene delivery to healthy, surrounding tissue. Furthermore, the integrin $\alpha_v\beta_3$ is expressed on proliferating endothelial cells (Brooks et al., Science, 264, 569–571 (1994); Brooks et al., Cell, 79, 1157–1165 (1994)). Targeting the $\alpha_v\beta_3$ receptor on these cells can be useful in preventing their proliferation, such as in reduction of tumor growth or treatment of retinal disease, or to promote further vascularization, such as the promotion of revascularization of ischemic tissue.

Moreover, other cells, such as those cells which adenovirus typically does not infect, can be targeted using the method of the invention, for instance, by targeting attachment of the adenovirus to cellular receptors on those cells or by increasing the efficiency of entry (i.e., specificity) into these cells. This can be accomplished by a variety of means, preferably by using a bispecific or multispecific binding agent, such as an antibody, that attaches an adenovirus to a particular cellular receptor.

Other applications of the method and constituents of the present invention will be apparent to those skilled in the art.

Means of Administration

The vectors of the present invention can be employed to contact cells either in vitro or in vivo. According to the invention "contacting" comprises any means by which cell entry of a vector is effected; the method is not dependent on any particular means of introduction and is not to be so construed. Means of introduction are well known to those skilled in the art, and also are exemplified herein.

Accordingly, introduction can be effected, for instance, either in vitro (e.g., in an ex vivo type method of gene therapy or in tissue culture studies) or in vivo by electroporation, transformation, transduction, conjugation or triparental mating, (co-)transfection, (co-)infection, membrane fusion with cationic lipids, high velocity bombardment with DNA-coated microprojectiles, incubation with calcium phosphate-DNA precipitate, direct microinjection into single cells, and the like. Similarly, the vectors can be introduced by means of cationic lipids, e.g., liposomes. Such liposomes are commercially available (e.g., Lipofectin®, Lipofectamine™, and the like, supplied by Life Technologies, Gibco BRL, Gaithersburg, Md.). Moreover, liposomes having increased transfer capacity and/or reduced toxicity in vivo (see, e.g., PCT international patent application no. WO 95/21259) can be employed in the present invention. Other methods also are available and are known to those skilled in the art.

One skilled in the art will appreciate that suitable methods of administering a vector (particularly an adenoviral vector) of the present invention to an animal for purposes of gene therapy (see, for example, Rosenfeld et al., Science, 252, 431–434 (1991); Jaffe et al., Clin. Res., 39(2), 302A (1991); Rosenfeld et al., Clin. Res., 39(2), 311A (1991); Berkner, BioTechniques, 6, 616–629 (1988)), chemotherapy, and vaccination are available, and, although more than one route can be used for administration, a particular route can provide a more immediate and more effective reaction than another route. Pharmaceutically acceptable excipients also are well-known to those who are skilled in the art, and are readily available. The choice of excipient will be determined in part by the particular method used to administer the vector. Accordingly, there is a wide variety of suitable formulations for use in the context of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, emulsions, gels, and the like containing, in addition to the active ingredient, such excipients as are known in the art.

A vector of the present invention, alone or in combination with other suitable ingredients, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressurized preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, a vector of the present invention can be made into suppositories by mixing with a variety of bases such as emulsifying bases or water-soluble bases.

Formulations suitable for vaginal administration can be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the gene of interest, the composition employed, the method of administration, and the particular site and organism being treated. However, preferably, a dose corresponding to an effective amount of a vector (e.g., an adenoviral vector according to the invention) is employed. An "effective amount" is one that is sufficient to produce the desired effect in a host, which can be monitored using several end-points known to those skilled in the art. For instance, one desired effect is nucleic acid transfer to a host cell. Such transfer can be monitored by a variety of means, including, but not limited to, a therapeutic effect (e.g., alleviation of some symptom associated with the disease, condition, disorder or syndrome being treated), or by further evidence of the transferred gene or coding sequence or its expression within the host (e.g., using the polymerase chain reaction, Northern or Southern hybridizations, or transcription assays to detect the nucleic acid in host cells, or using immunoblot analysis, antibody-mediated detection, or particularized assays to detect protein or polypeptide encoded by the transferred nucleic acid, or impacted in level or function due to such transfer). These methods described are by no means all-inclusive, and further methods to suit the specific application will be apparent to the ordinary skilled artisan.

Generally, to ensure effective transfer of the vectors of the present invention, it is preferable that about 1 to about 5,000 copies of the adenoviral vector according to the invention be employed per cell to be contacted, based on an approximate number of cells to be contacted in view of the given route of administration, and it is even more preferable that about 3 to about 300 pfu enter each cell. However, this is merely a general guideline, which by no means precludes use of a higher or lower amount, as might be warranted in a particular application, either in vitro or in vivo. For example, the actual dose and schedule can vary depending on whether the composition is administered in combination with other pharmaceutical compositions, or depending on interindividual differences in pharmacokinetics, drug disposition, and metabolism. Similarly, amounts can vary in in vitro applications depending on the particular cell type targeted or the means by which the vector is transferred. One skilled in the art easily can make any necessary adjustments in accordance with the necessities of the particular situation.

EXAMPLES

The following examples serve to illustrate the present invention and are not intended to limit its scope in any way.

With respect to the following examples:

All DNA manipulations were performed in accordance with standard protocols (Ausubel et al., *Current Protocols in Molecular Biology*, Greene Publishing Assocs./Wiley-Interscience, New York (1989)).

Protein analysis through SDS-PAGE and Western blotting also were performed in accordance with published protocols (Ausubel et al., supra; and Laemmli, *Nature*, 227, 680–685 (1970)).

Ad2, Ad3, Ad5 and Ad9 were obtained as stocks from the ATCC (Rockville, Md.) and were passaged on A549 or HeLa cells in Dulbecco's Minimal Essential Medium (DMEM; Gibco BRL, Gaithersburg, Md.) supplemented with 5% fetal calf serum (FCS).

The HepG2, Hs 700T, A172, U118, and Tera 2 cell lines were obtained from ATCC and were maintained in DMEM supplemented with 5% FCS.

The Ramos and Y79 cell lines also were obtained from the ATCC and were maintained in RPMI (Gibco BRL) with 5% FCS.

Human aortic smooth muscle cells (HASMS) were purchased from Cell Systems Corp. (Kirklans, Wash.) and were maintained in MCDB (Gibco BRL) with 5% FCS.

Human melanoma ACA19 cells were a gift from John Hilkens (Netherlands Cancer Institute, Amsterdam) and maintained in DMEM with 5% FCS.

Hamster melanoma CS-1 cells were a gift from Caroline Damsky (Schools of Dentistry and Medicine, UCSF, San Francisco, Calif.).

The β5 integrin subunit gene was obtained from Sarah Bodary (Genentech Inc., South San Francisco, Calif.).

The CS-1 cells and derivatives thereof were maintained in DMEM with 5% FCS.

$^3$H-methyl-thymidine-labeled adenoviruses were obtained by infecting A549 monolayers (approximately 12 million cells/flask) at a multiplicity of infection (moi) of 5. At 24 hr postinfection (pi), 0.5 mCi of $^3$H-methyl-thymidine were added in a volume of 10 ml. After overnight incubating in this low volume, 15 ml of medium were added and cells were harvested at 55–96 hr pi. The cells were then pelleted, washed twice, and resuspended in DMEM with 10 mM Tris, pH=8.0. Virus was released from cells by three freeze/thaw cycles and the cellular debris was removed by centrifugation. The supernatant was layered onto a CsCl gradient and centrifuged for 5 hr at 22,500 rpm. Banded virus was collected and dialyzed overnight against 10 mM Tris, pH=8.0, 150 mM NaCl, 10 mM MgCl$_2$ and 10% glycerol. The dialysate was aliquoted and stored at −80° C. until further use.

Example 1

This example describes the production and purification of adenoviral proteins.

The fiber sequences of Ad3 (GenBank accession no. M12411; Signaes et al. (1985), supra), Ad5 (GenBank accession no. M18369; Chroboczek et al. (1992), supra; and Chroboczek et al., Virol., 161, 549–554 (1987)), and Ad9 (GenBank accession no. X74659) were used to design primers to amplify fiber knobs from adenoviral genomic DNA. The primers were designed such that they included a Bam HI site on the sense primer and a Kpn I site on the antisense primer in order to facilitate cloning of the PCR product after digestion with the appropriate restriction enzymes. The sense primers were designed to hybridize such that, upon amplification, the product would include the ultimate repeat of the shaft of each target fiber gene, the conserved shaft-knob junction TLWT (Stouten et al., J. Molec. Biol., 226, 1073–1084 (1992); SEQ ID NO: 4) and the receptor-recognizing knob (Henry et al. (1994), supra; Louis et al., J. Virol., 68, 4104–4106 (1994); and Stevenson et al., J. Virol., 69, 2850–2857 (1995)). PCR reactions were performed using Ultma DNA polymerase (Perkin Elmer, Foster City, Cailf.), and a standard PCR protocol. The products were then cloned as Bam HI/Kpn I fragments in the bacterial expression vector pQE32 (Qiagen Inc., Chatsworth, Cailf.). The DNA sequence of the fiber knobs was determined using an automated 373 DNA sequencer (Applied Biosystems, Foster City, Cailf.), and no sequence differences were found in comparison with the original sequences reported in the Genbank database.

The pQE32 vector was then cut with the restriction enzymes Eco RI and Kpn I to release the complete insert, which was then cloned into the baculoviral transfer vector pAcSG2 (Pharmingen, San Diego, Cailf.). Recombinant baculoviruses containing the Ad3, Ad5 or Ad9 fiber knob constructs were isolated and amplified according to standard protocols (O'Reilly et al., Baculovirus expression vectors: a laboratory manual, W. H. Freeman & Co., Salt Lake City, Utah (1992)). Recombinant Ad2, Ad3, Ad5 and Ad9 fibers were produced and purified as described previously (Wickham et al. (1993), supra). Ad3, Ad5 and Ad9 knob proteins (F3K, F5K and F9K, respectively) were produced in high yields in Tn5 B1-4 insect cells (Invitrogen, San Diego, Cailf.) and were easily purified to homogeneity using Ni$^{2+}$ NTA agarose columns as described by the manufacturer (Qiagen). Protein gel analysis revealed bands that migrated at the expected sizes of 24.1 kDa for F3K, 23.5 kDa for F5K, and 24.3 kDa for F9K. Western blot analysis showed that both F5K and F9K cross-reacted with a rabbit polyclonal antibody raised against the fiber 2 protein, whereas F3K did not. $^{35}$S-labeled Ad3, Ad5 and Ad9 fiber knobs were produced as previously described (Wickham et al. (1993), supra).

Example 2

This example demonstrates the cross-competition of Ad2, Ad5 and Ad9 for the same cellular fiber receptor on A549 cells.

Approximately 1×10$^6$ A549 cells in 250 μl of Dulbecco's phosphate-buffered saline (PBS; Gibco BRL) with 3 mM MgCl$_2$ and 1 mM CaCl$_2$ (PBS$^{++}$) were preincubated for 1 hr at 4° C. with increasing numbers of viral particles in Eppendorf tubes precoated with 5% bovine serum albumin (BSA) in PBS$^{++}$. Recombinant fiber knobs were added to the cell suspensions at final concentrations of 10 μg/ml, and the suspensions then were incubated at 37° C. for 1 hr and, subsequently, chilled for 15 min at 4° C. Labeled virus or labeled fiber protein (1–3×10$^4$ cpm) was then added to the cell suspensions, which were incubated at 4° C. for an additional hour. After incubation, the cells were pelleted, the inoculum was removed, and the pellet was washed twice with cold PBS$^{++}$. The pellet was resuspended in 100 μl of PBS$^{++}$, added to scintillation fluid, and counted directly in a Beckman scintillation counter.

Figure 1A:
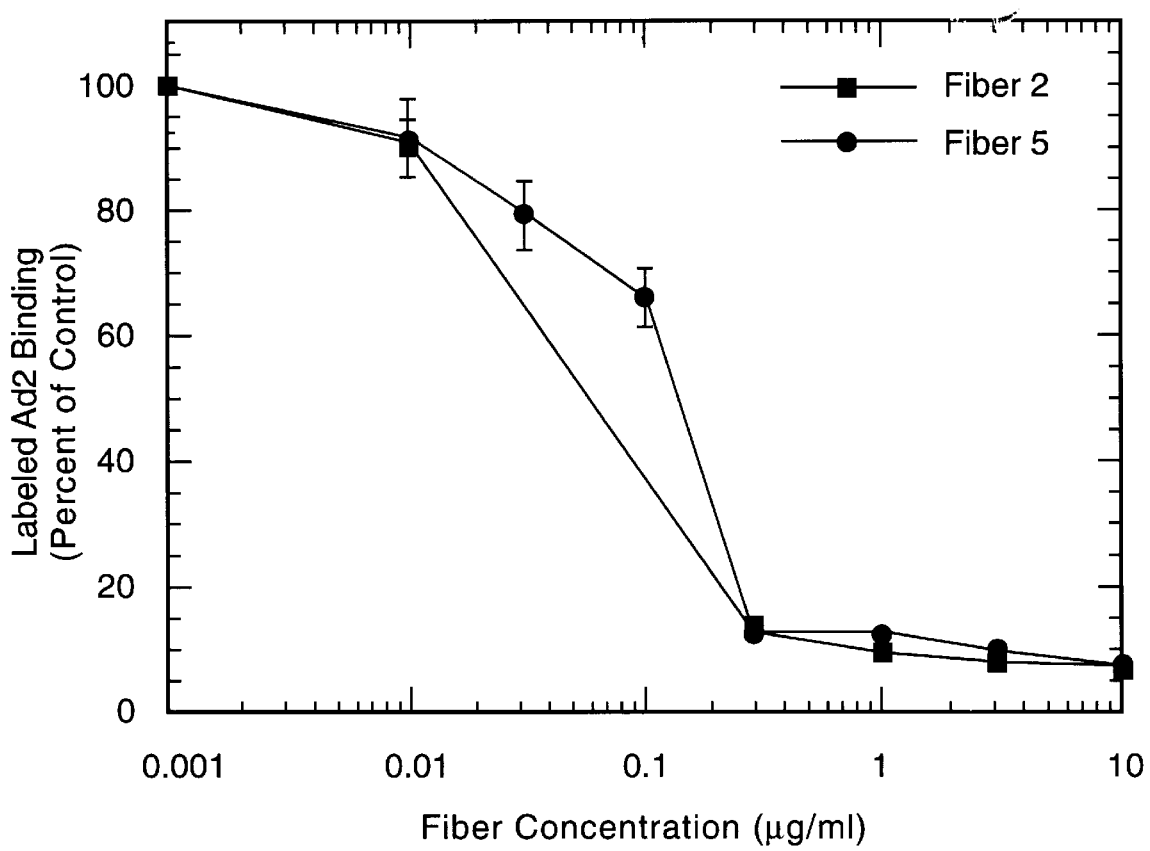
FIG. 1A is a graph of labeled Ad2 binding (% of control) versus fiber concentration (μg/ml) in the presence of competing unlabeled fiber 2 (■) and unlabeled fiber 5 (•).
Figure 1B:
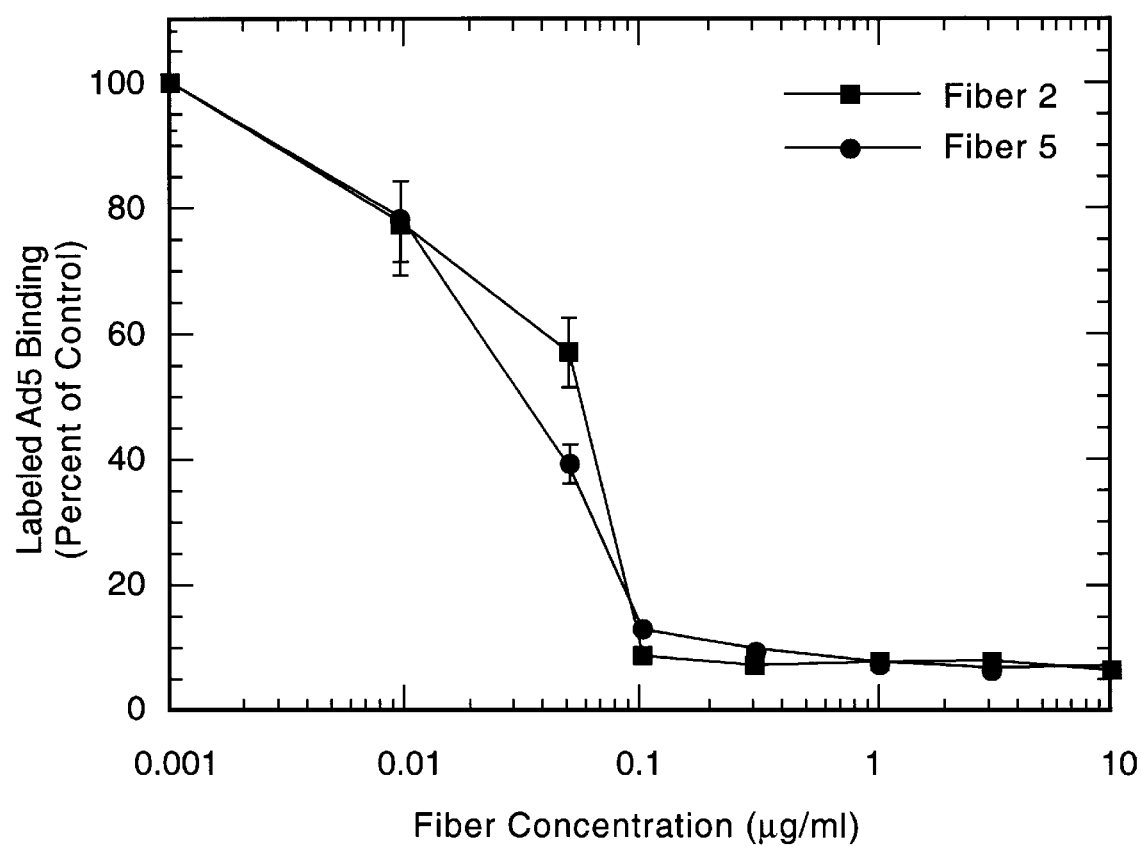
FIG. 1B is a graph of labeled Ad5 binding (% of control) versus fiber concentration (μg/ml) in the presence of competing unlabeled fiber 2 (■) and unlabeled fiber 5 (•).

Increasing amounts of full-length recombinant fiber 2 and fiber 5 inhibited comparably the binding of both Ad2 and Ad5 as shown in FIGS. 1A and 1B, respectively. FIGS. 1A and 1B are graphs of labeled Ad2 and labeled Ad5 binding (% of control), respectively, versus fiber concentration (μg/ml) in the presence of competing unlabeled fiber 2 (■) and unlabeled fiber 5 (•). In both cases, saturation of the receptor sites, with a maximum inhibition of labeled viral binding of 95%, occurred between final concentrations of 0.1 and 0.3 μg/ml. Therefore, fiber-mediated homotypic (same serotype) and heterotypic (same subgroup) cross-competition occurred between serotypes Ad2 and Ad5, which suggested that the Ad2 and Ad5 fibers recognized the same receptor. This also suggested that the fibers could be used interchangeably as competitors in Ad2 and Ad5 viral binding studies.

Cross-competition between serotypes of different subgroups, i.e., Ad2 (subgroup C), Ad3 (subgroup B), and Ad9 (subgroup D), was examined by using receptor-recognizing recombinant fiber knobs, instead of the complete fiber proteins, as competitors. His-tagged F3K, F5K, and F9K were generated as described in Example 1.

Figure 2A:
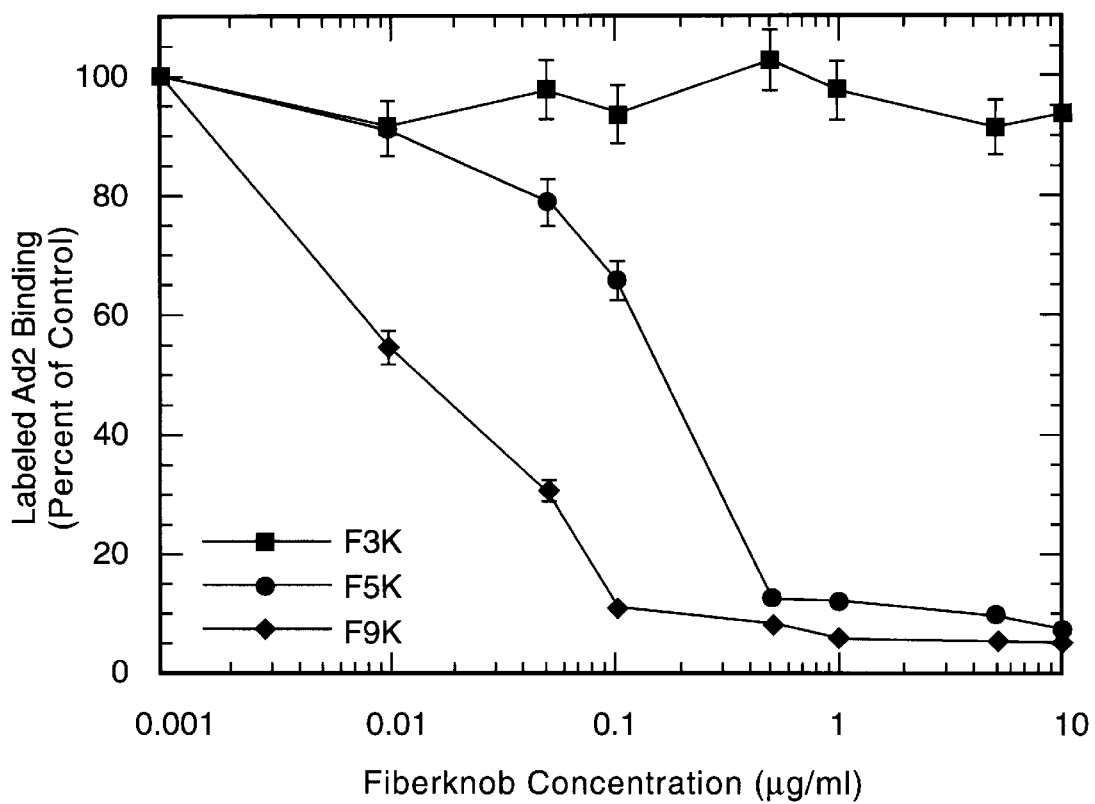
FIG. 2A is a graph of labeled Ad2 binding (% of control) versus fiber knob concentration (μg/ml) in the presence of competing unlabeled fiber 3 knob (F3K) (■), fiber 5 knob (F5K) (•), and fiber 9 knob (F9K) (♦).

Preincubation of A549 cells with increasing amounts of F3K, F5K or F9K resulted in a dose-dependent inhibition of labeled Ad2 binding with F5K and F9K, but not F3K as shown in FIG. 2A, which is a graph of labeled Ad2 binding (% of control) versus fiber knob concentration (μg/ml) in the presence of competing unlabeled F3K (■), F5K (•), and F9K (♦). At a concentration of 1 μg/ml, more than 90% of Ad2 binding was inhibited. These experiments suggested that the F9K protein competed for the same receptor site as did the F5K protein. The F3K protein, which was used as a control in this binding experiment, had no effect on Ad2 binding.

Figure 2B:
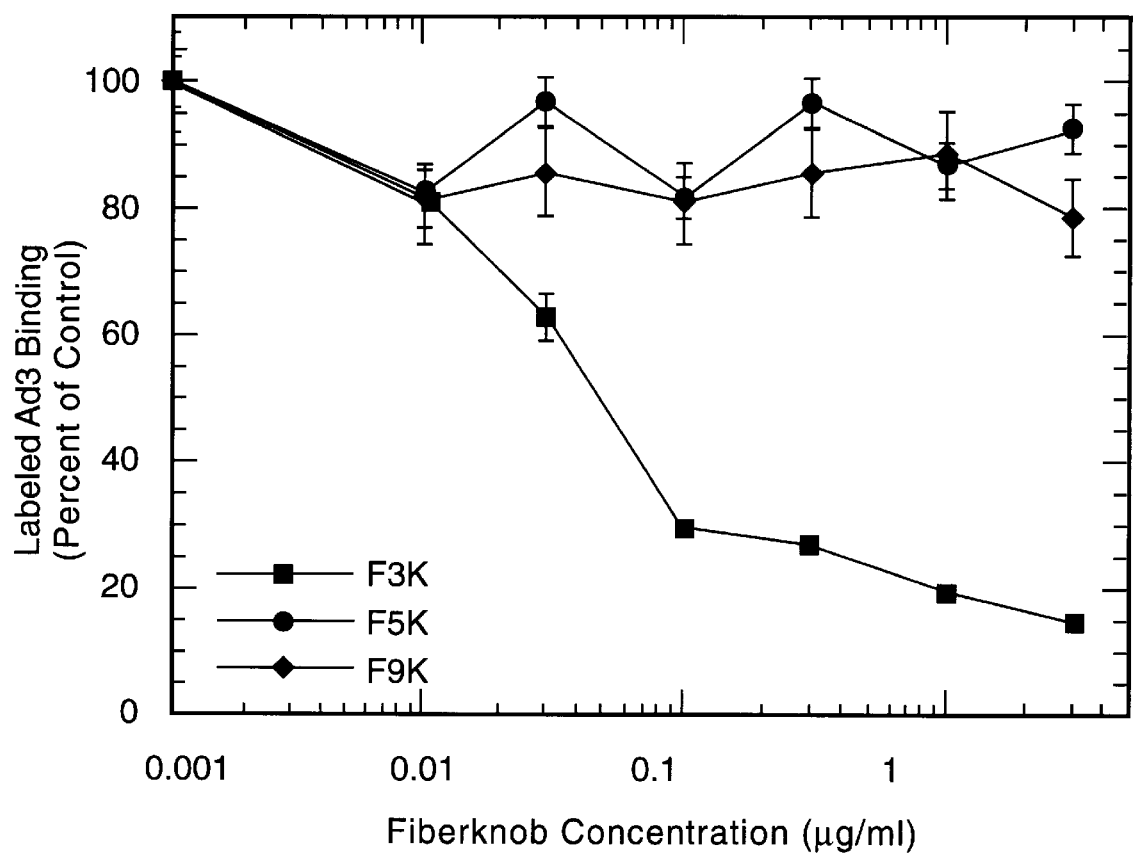
FIG. 2B is a graph of labeled Ad3 binding (% of control) versus fiber knob concentration (μg/ml) in the presence of competing unlabeled F3K (■), F5K (•), and F9K (♦).

Preincubation of A549 cells with increasing amounts of F3K, F5K or F9K, followed by incubation with labeled Ad3, showed that only the homologous fiber knob had a maximum inhibitory effect of 8596 on Ad3 binding at the highest doses tested as shown in FIG. 2B, which is a graph of labeled Ad3 binding (% of control) versus fiber knob concentration (μg/ml) in the presence of competing unlabeled F3K (■), F5K (•), and F9K (♦). Further preincubation of cells with a combination of F3K and penton base protein or the monoclonal antibody L230, which is directed against α$_v$ integrins (Weinacker et al., J. Biol. Chem., 269, 6940–6948 (1994)), led to complete inhibition of Ad3 binding. Neither F5K nor F9K had any effect on Ad3 binding. These results confirmed that Ad3 recognized a receptor other than the Ad2/Ad5 receptor and also showed that Ad3 can make use of its penton base to interact directly with $\alpha_v$ integrins.

Figure 2C:
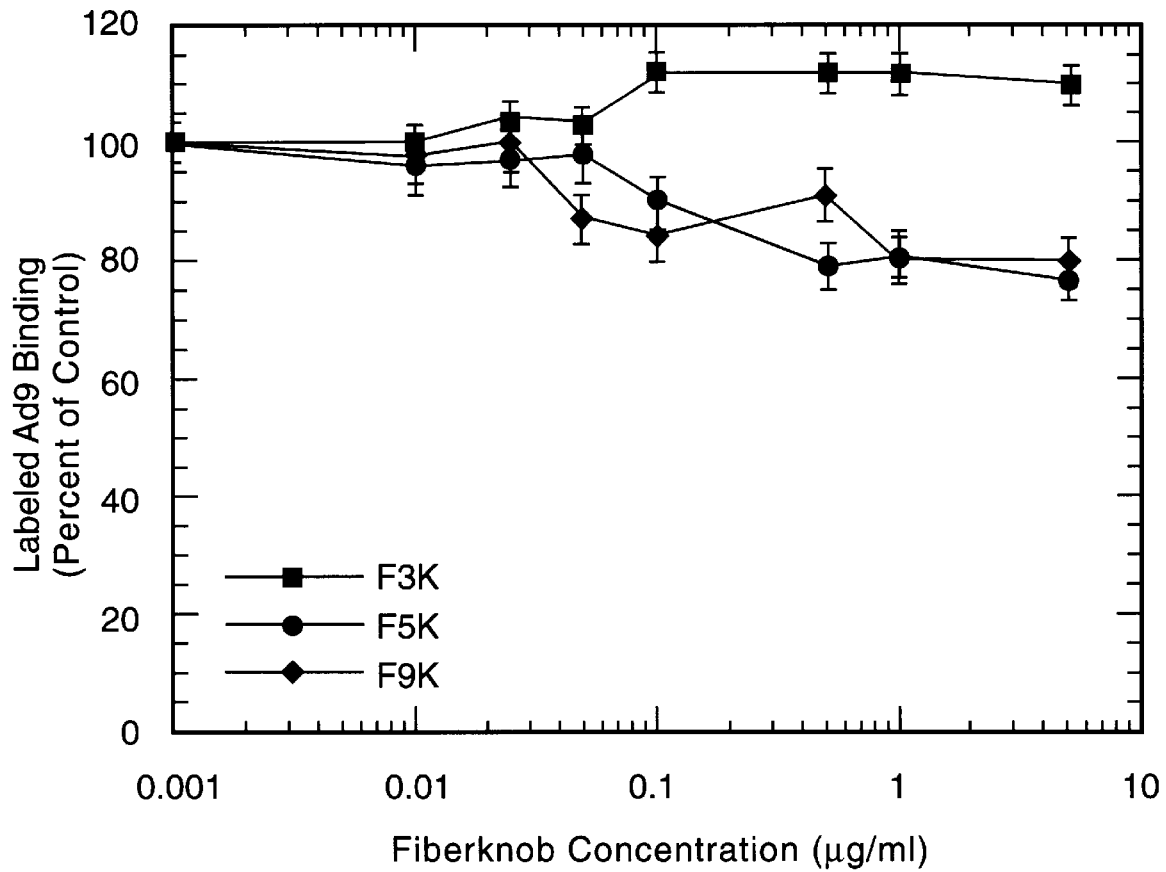
FIG. 2C is a graph of labeled Ad9 binding (% of control) versus fiber knob concentration (μg/ml) in the presence of competing unlabeled F3K (■), F5K (•), and F9K (♦).

Preincubation of A549 cells with increasing amounts of F3K, F5K or F9K, followed by incubation with labeled Ad9, showed that the latter two knobs, at the highest concentration used, had a maximum inhibitory effect of 20% on viral binding as shown in FIG. 2C, which is a graph of labeled Ad9 binding (% of control) versus fiber knob concentration (μg/ml) in the presence of competing unlabeled F3K (■), F5K (•), and F9K (♦). In fact, in competition experiments with the two epithelial cell lines A549 and Hs 700T, using end concentrations of up to 25 μg/ml, no further inhibition was observed. These results suggest that Ad9 can attach to A549 and Hs 700T cells by employing a fiber-independent mechanism.

Figure 3A:
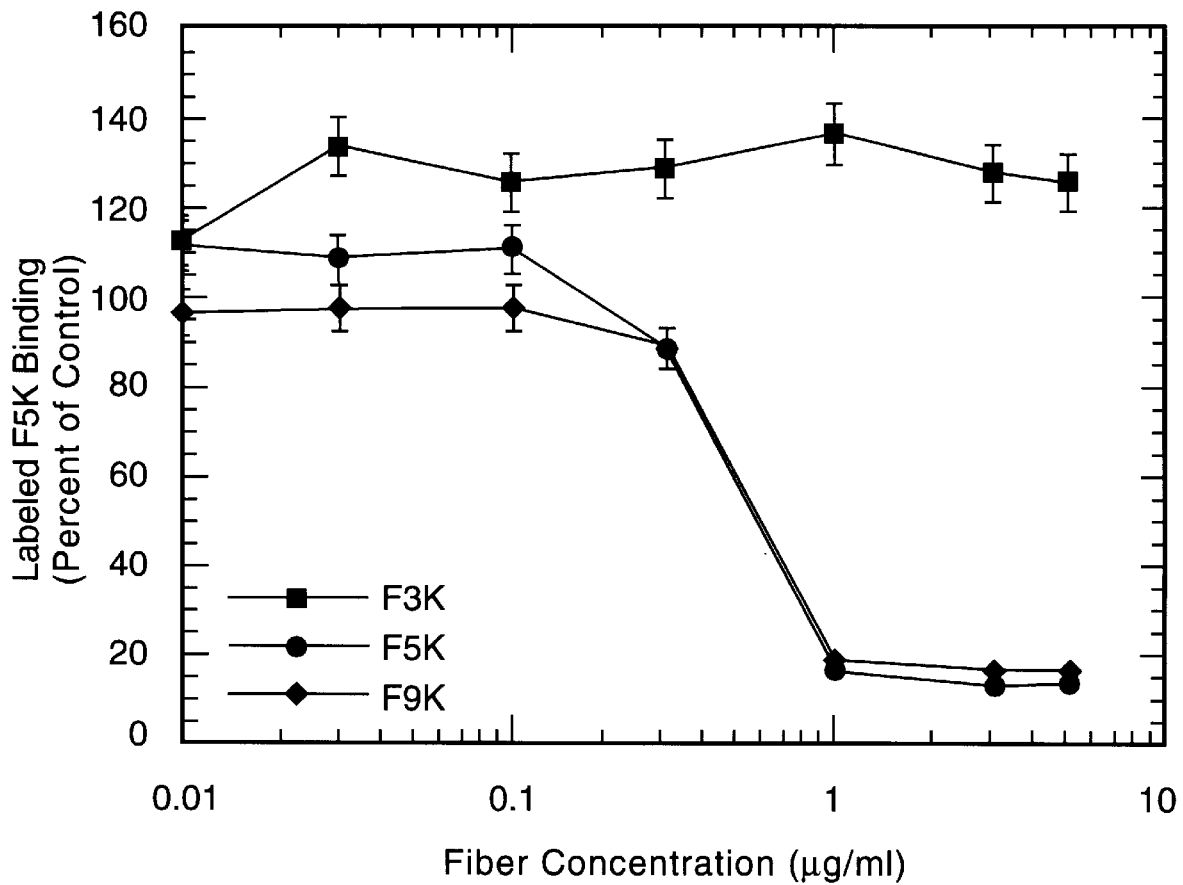
FIG. 3A is a graph of labeled F5K binding (% of control) versus fiber concentration (μg/ml) in the presence of competing unlabeled F3K (■), FSK (•), and F9K (♦).
Figure 3B:
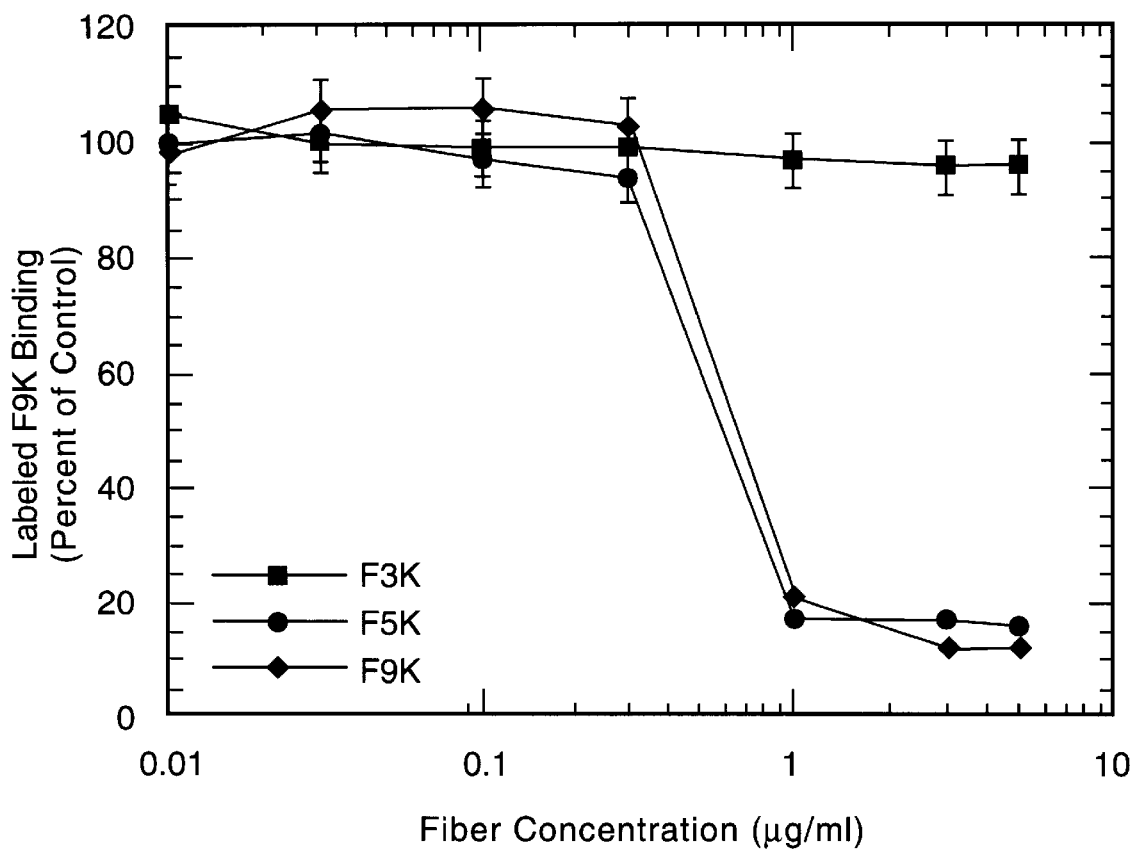
FIG. 3B is a graph of labeled F9K binding (% of control) versus fiber concentration (μg/ml) in the presence of competing unlabeled F3K (■), F5K (•), and F9K (♦).

Direct protein-protein competition experiments for the fiber receptor on A549 cells were set up with $^{35}$S-labeled F5K and unlabeled F5K or F9K and vice versa in order to determine whether or not the inhibition of Ad2 binding was due to competition for the Ad2/Ad5 fiber receptor. Both competitors competed for the binding sites of labeled F5K with identical affinity as shown in FIG. 3A, which is a graph of labeled F5K binding (% of control) versus fiber concentration (μg/ml) in the presence of competing unlabeled F3K (■), F5K (•), and F9K (♦). Complete competition of labeled F5K binding occurred upon preincubation of the cells with between 300 ng/ml and 1 μg/ml of unlabeled F5K or F9K. With labeled F9K, the unlabeled competitors also competed in a similar fashion as shown in FIG. 3B, which is a graph of labeled F9K binding (% of control) versus fiber concentration (μg/ml) in the presence of competing unlabeled F3K (■), F5K (•), and F9K (♦).

Also, in virus/virus competition experiments, preincubation of A549 cells with increasing numbers of unlabeled Ad9 virions per cell resulted in a dose-dependent decrease in binding of labeled Ad2 virions. The virus/virus, fiber/virus, and fiber/fiber cross-competition data all strongly suggest that F5K and F9K recognize the same or similar receptor.

Example 3

This example demonstrates that Ad2 and Ad9 bind directly to $\alpha_v$ integrins by way of the penton base protein.

Figure 4A:
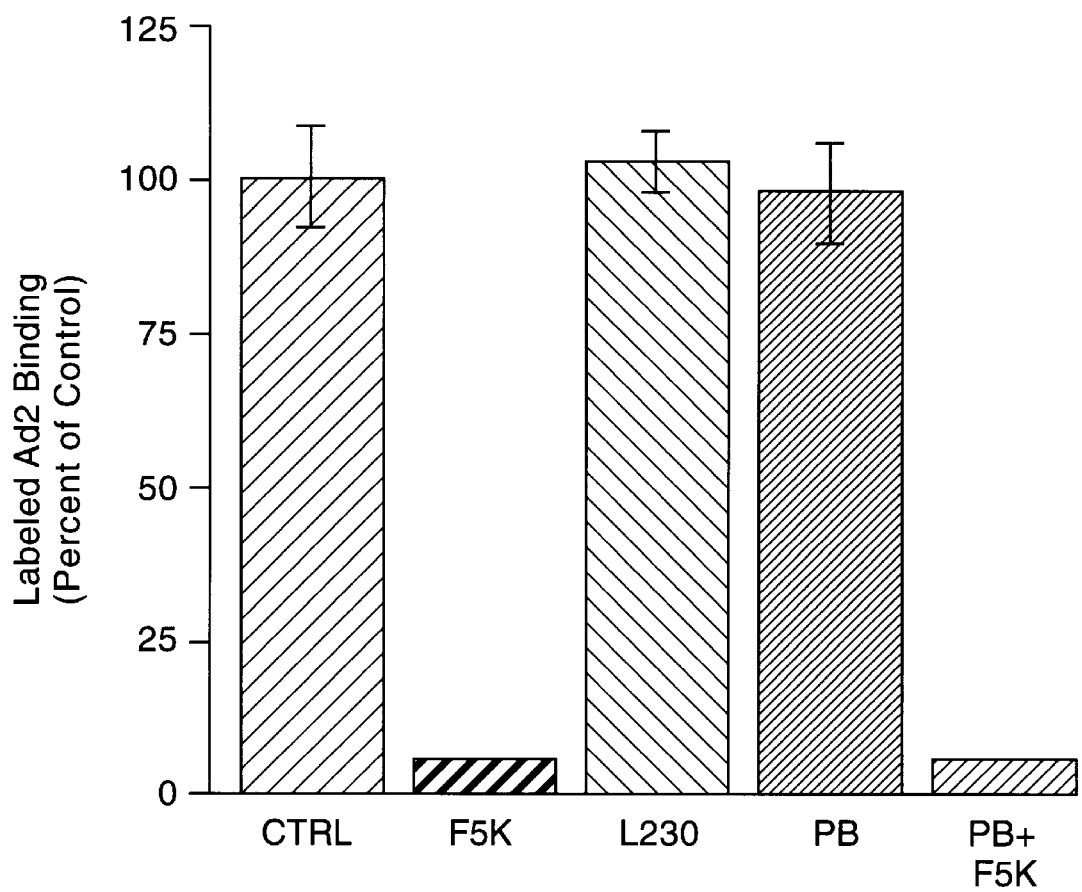
FIG. 4A is a bar graph of labeled Ad2 binding (% of control) versus control (CTRL), F5K, the monoclonal antibody (mAb) L230, penton base (PB), and PB plus F5K.

Hs700T cells were preincubated with either F5K or F9K (at a final concentration of 2 μg/ml), which will inhibit Ad2 or Ad9 fiber binding, respectively, the mAb L230 (at a final concentration of 50 μg/ml), which will functionally block direct penton/$\alpha_v$ integrin interaction, the Ad2 penton base, or the Ad2 penton base with the relevant fiber knob. Next, $1-3\times10^4$ cpm of labeled Ad2 or Ad9 were added and the mixture was incubated for 1 hr at 4° C. Cells were pelleted and washed twice with cold PBS$^{++}$. Cell-associated cpm were then determined in a scintillation counter (binding percentage=counts of input dose bound to cells/precise cpm of input dose). Determination of bound virus showed that Ad2 binding was inhibited by more than 95%o by F5K as shown in FIG. 4A, which is a bar graph of labeled Ad2 binding (% of control) versus CTRL, F5K, L230, PB, and PB plus F5K (std. dev. of mean≦7%). Preincubation of the cells with saturating amounts of L230 or Ad2 penton base had no effect on Ad2 binding. A combination of penton base with F5K showed no additive inhibitory effect on Ad2 binding, which confirmed that only fiber mediates the initial Ad2 binding to Hs 700T cells and other epithelial cell lines, like A549, as shown in Table I.

TABLE 1

Binding of Ad2 and Ad9 to cell lines expressing various levels of fiber receptor and $\alpha_v$ integrins

| Cell-Line** | Fiber Receptor | Integrins* | Ad2 | | | Ad9 | | |
|---|---|---|---|---|---|---|---|---|
| | | | Ctrl (%) | F5K (%) | L230 (%) | Ctrl (%) | F9K (%) | L230 (%) |
| A549 | ++ | + | 10.6 | 0.8 | 10.0 | 9.7 | 7.8 | 6.0 |
| HepG2 | ++ | + | 10.0 | 0.9 | 10.0 | 1.5 | 1.8 | 1.1 |
| Hs 700T | ++ | + | 6.9 | 0.5 | ND | 9.5 | 7.3 | 5.1 |
| A172 | +/− | + | 3.0 | 1.7 | 3.0 | 2.4 | 2.4 | 1.1 |
| ACA19 | +/− | + | 2.1 | 1.1 | ND | 2.3 | 2.3 | 0.4 |
| HASMC | +/− | + | 1.1 | 0.6 | 1.3 | 2.6 | 4.3 | 0.5 |
| U-118 MG | +/− | + | 2.2 | 2.0 | ND | 0.9 | 1.0 | 0.4 |
| Ramos | ++ | − | 11.6 | 1.0 | 10.5 | 1.4 | 0.2 | 1.4 |
| Y79 | +++ | − | 28.2 | 0.94 | 26.2 | 3.2 | 1.3 | 3.3 |
| Tera 2 | +++ | + | 43.4 | 1.3 | 41.2 | 6.4 | 1.9 | 3.3 |

*Integrins: the vitronectin receptors $\alpha_v\beta_3$ and $\alpha_v\beta_5$ ND: Not determined
**The cell lines and derivations are: A549, human lung carcinoma; HepG2, hepatocarcinoma; Hs 700T, metastatis of an intestinal or pancreatic carcinoma: A172 and U-118-MG, glioblastomas; ACA19, human melanoma cell line; HASMC, Human Aortic Smooth Muscle Cells; Ramos, human lymphoma; Y79, retinoblastoma; and Tera 2, embryonic teratocarcinoma.

Figure 4B:
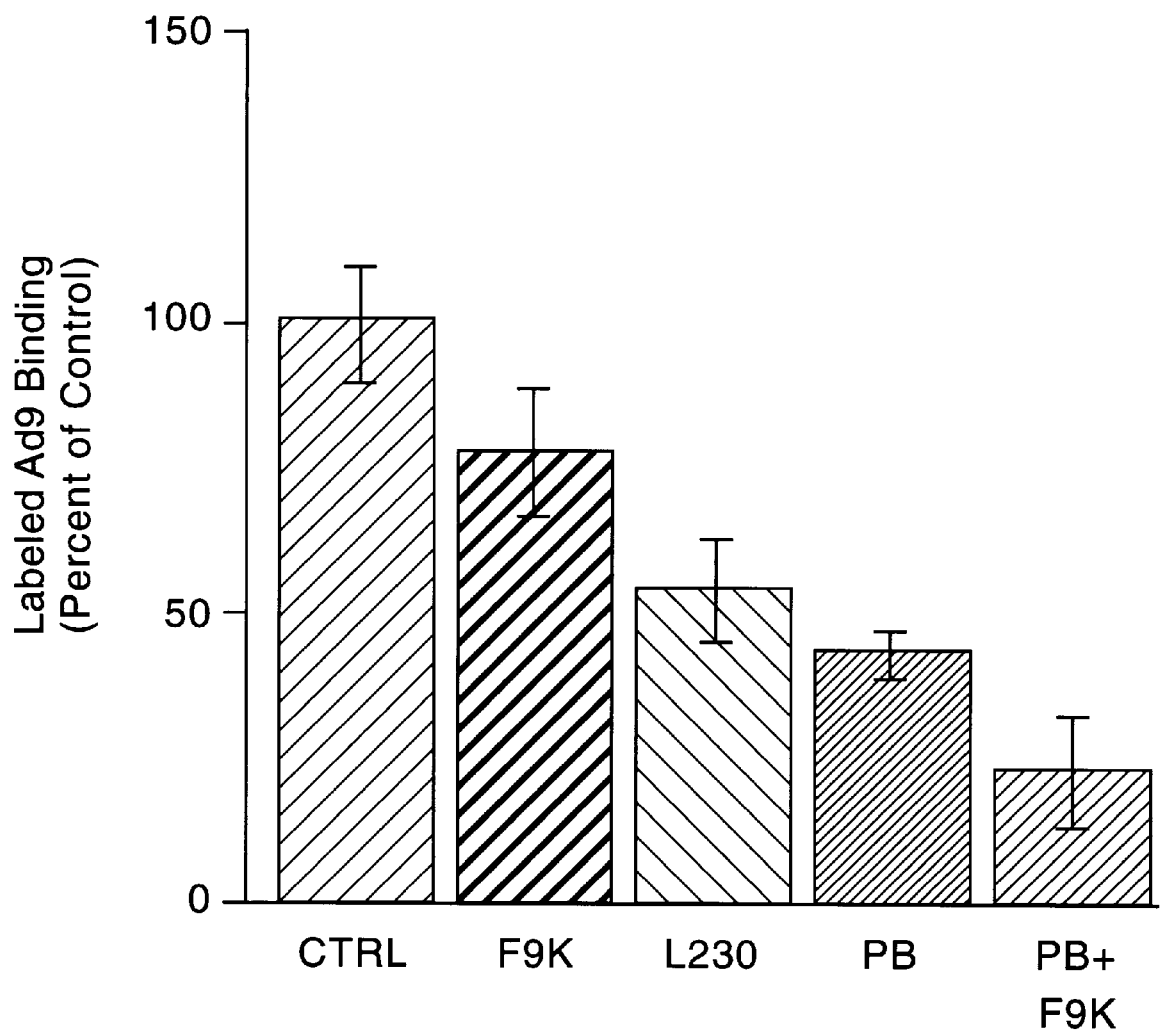
FIG. 4B is a bar graph of labeled Ad9 binding (% of control) versus CTRL, F9K, L230, penton base (PB), and PB plus F9K.

Binding of Ad9 was blocked by 20–25% by F9K, 46% by L230, 57% by Ad2 penton base, and 77% by Ad2 penton base and F9K combined as shown in FIG. 4B, which is a bar graph of labeled Ad9 binding (% of control) versus CTRL, F9K, L230, PB, and PB plus F9K. These results confirmed that Ad9 could bind to cells independent of fiber-receptor interactions, by employing a mechanism, such as direct interaction of penton base with $\alpha_v$ integrins, which has been shown here to play a predominant role in Ad9 attachment and binding to Hs 700T cells and other epithelial cell lines, e.g., line A549, as shown in Table I above. These results, however, do not exclude the possibility that proteins other than fiber or penton base play a minor role in viral attachment and binding to the cell surface.

Example 4

This example demonstrates that soluble fiber protein does not block cellular infection by Ad9.

Approximately $10^6$ Hs 700T cells per well were seeded and left to attach. The medium (DMEM plus 10% FCS) was removed and the cells washed twice with PBS$^{++}$. The fiber 5 and fiber 9 knobs and the Ad2 penton base were then added to the wells at a final concentration of 10, 10 and 50 μg/ml, respectively, in DMEM without FCS, and the cells were incubated for 2 hr at 4° C. Virus was added at dilutions previously determined to generate statistically reliable numbers of foci, and the cells were incubated for another 1.5 hrs in the cold. The inoculum was removed and the wells were washed twice with cold DMEM without FCS. Two mls of DMEM with 10% FCS were added, and the cells were incubated for 24–48 hr. The adenoviral infection was quantitated as described in Wickham et al. (1993), supra, with the following modifications. Briefly, cell monolayers were fixed with 2% paraformaldehyde in PBS for 20 min, followed by two washes with PBS and a 5 min incubation with 0.2% Triton X-100. The cells were washed twice with 0.5% fish gelatin (Sigma, St. Louis, Mo.) in PBS and then blocked with the same solution for one hour. Primary antibodies directed against the adenoviral DNA binding protein and the hexon protein (both provided by Douglas Brough, GenVec, Inc.) or the penton base protein (provided by Glen Nemerow, The Scripps Institute) were used in dilutions of 1:100 to 1:250 in PBS with 0.5% fish gelatin and incubated for 1 hr. Cells were washed three times and incubated overnight with a 1:100 dilution of FITC-conjugated goat anti-rabbit antibody (Boehringer Mannheim, Indianapolis, Ind.) in PBS with 0.5% fish gelatin. After three washes, 1 ml of PBS was put over the stained cells, and foci were counted using a Nikon Diaphot 200 fluorescence microscope.

Figure 5A:
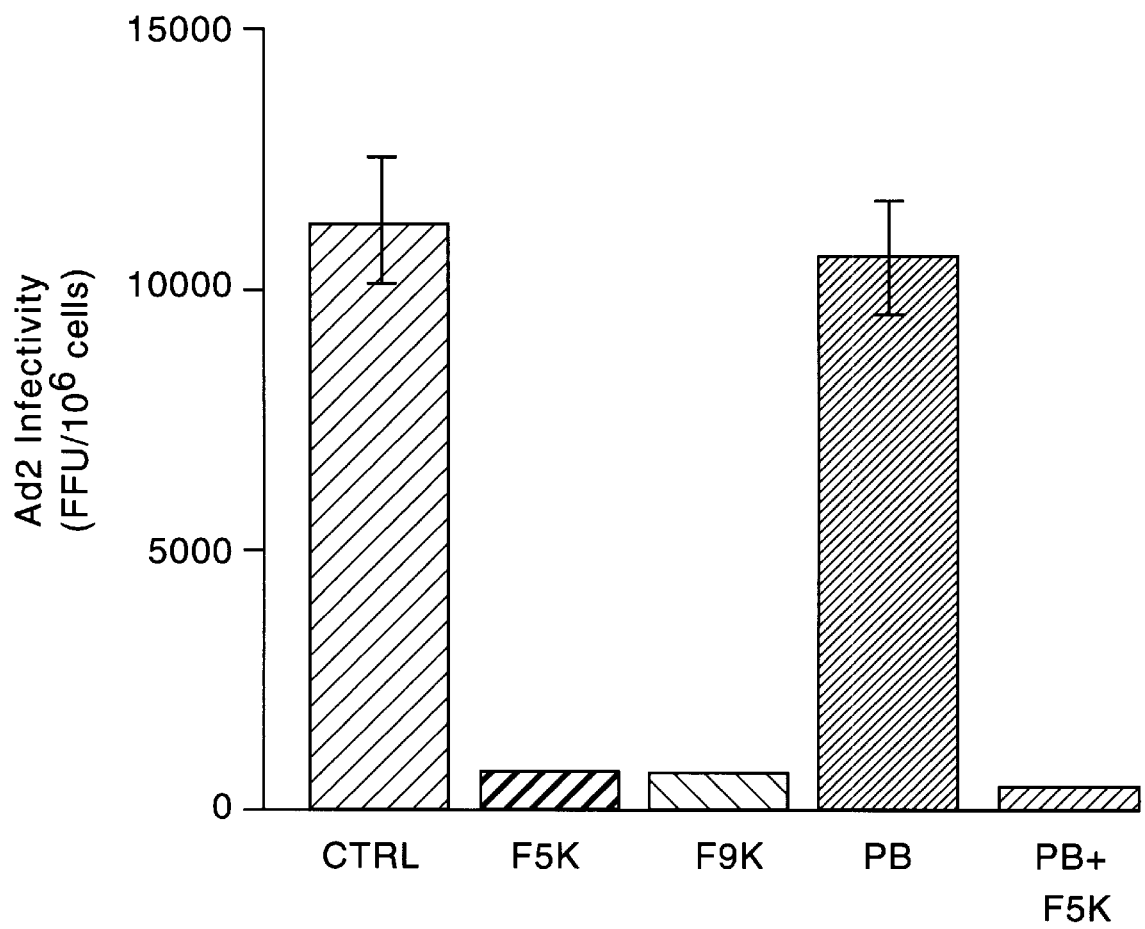
FIG. 5A is a bar graph of Ad2 infectivity (FFU/$10^6$ cells) versus CTRL, F5K, F9K, PB, and PB plus F5K, for an experiment performed in duplicate with anti-PB antibody.

The effect of competitors on the infection of Hs 700T cells by unlabeled Ad2 and Ad9 was analyzed using antibodies that detect proteins specific to both the early (α-DNA binding protein) and late phase (α-hexon and α-penton base) of the adenoviral infection cycle. Analysis of the Ad2 infection with the three described antibodies showed total abrogation by preincubation of the cells with both fiber knobs as shown in FIG. 5A, which is a bar graph of Ad2 infectivity (FFU/$10^6$ cells) versus CTRL, F5K, F9K, PB, and PB plus F5K, for an experiment performed in duplicate with anti-PB antibody. No effect was observed for preincubation with saturating amounts of Ad2 penton base protein.

Figure 5B:
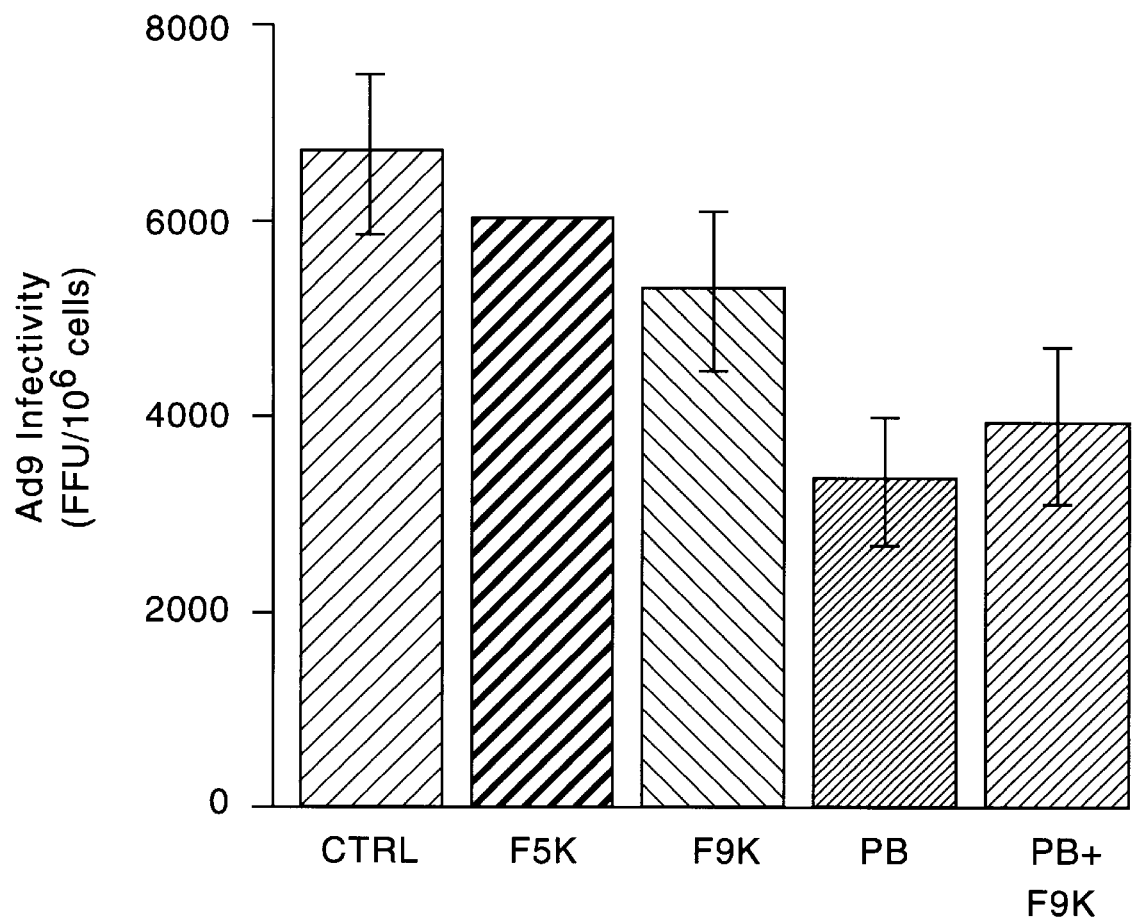
FIG. 5B is a bar graph of Ad9 infectivity (FFU/$10^6$ cells) versus CTRL, F5K, F9K, PB, and PB plus F5K, for an experiment performed in duplicate with anti-PB antibody.

Analysis of the Ad9 infection with the three described antibodies showed no significant inhibitory effect for F5K. Similarly, preincubation of the cells with F9K resulted in only a marginal but statistically insignificant inhibition of infectivity, as shown in FIG. 5B, which is a bar graph of Ad9 infectivity (FFU/$10^6$ cells) versus CTRL, F5K, F9K, PB, and PB plus F5K, for an experiment performed in duplicate with anti-PB antibody. Preincubation with saturating amounts of Ad2 penton base, however, resulted in a 45% decrease in the number of foci formed. These results show that Ad9 infection involves direct interaction of the penton base with the $\alpha_v$ integrins. The fact that competition with a combination of penton base and fiber does not further decrease infectivity suggests that Ad9 penton may interact with other cellular receptors.

Example 5

This example demonstrates that Ad9 can bind directly to $\alpha_v$ integrins.

Ad2 and Ad9 binding was further analyzed using a panel of human cell lines that display varying levels of fiber receptor and express or lack $\alpha_v$ integrins (see Table I). Two cell lines, the hepatocarcinoma-derived HepG2 and Hs 700T bound Ad2 at levels between 5 and 10% of input dose of labeled Ad2 virus used. These levels dropped by more than 90% when the cells were preincubated with saturating amounts of F5K, showing that the binding of Ad2 is fiber-dependent and specific. No effect was observed for L230, indicating that the penton base does not play an appreciable role in Ad2 binding. Ad9 binding to HepG2 was not inhibited by F9K, but was inhibited 25% by L230. Ad9 binding to Hs 700T was inhibited 25% by F9K. About 45% of Ad9 binding to Hs 700T involved interaction with the $\alpha_v$ integrins. Binding of Ad2 to A172, U118 MG, ACA19 and HASMC, all of which display low levels of Ad2 fiber receptor, was low. Ad9 binding to these cell lines was not significantly reduced by preincubation with F9K protein and, therefore, primarily involved direct penton/$\alpha_v$ integrin interactions, as confirmed by the drop in binding percentage upon preincubation of the cells with the mAb L230. Ad9 bound to Ramos and Y79, both of which express little or no $\alpha_v$ integrins, at low levels. About 60–80% of the bound virus appeared to bind to these cells via the fiber as evidenced by the binding percentage obtained upon preincubation with F9K protein. Neither Ramos nor Y79 showed any effect on binding by preincubation with L230. Ad9 also bound to Tera 2, which has $\alpha_v$ integrins and expresses extremely high levels of fiber receptor (as evidenced by the binding data for Ad2), primarily via the fiber, despite the presence of the $\alpha_v$ integrins, which may reflect the cellular fiber receptor density. Preincubation of Tera 2 cells with L230 had no effect on Ad9 binding. Fiber-mediated binding of Ad9 to HepG2, Ramos, Y79, and Tera 2 was about 6–9 fold lower than that of Ad2. These results suggest that adenoviral vectors with shortened fiber shafts will have a higher targeting specificity by decreasing the level of fiber-receptor-mediated binding.

Figure 6A:
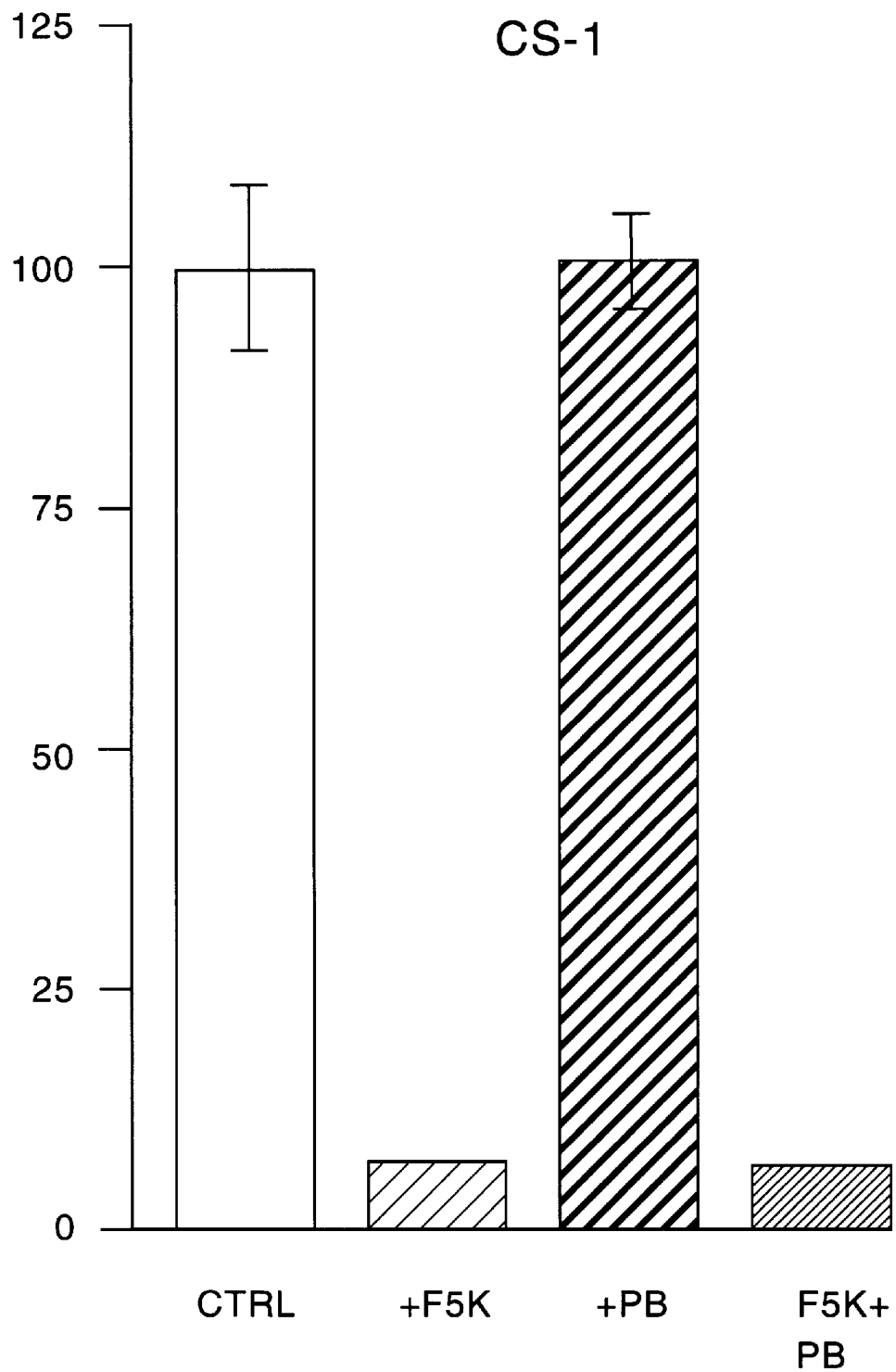
FIG. 6A is a graph of labeled Ad2 binding (% of control) versus CTRL, F5K, PB, and F5K plus PB for CS-1. Results shown are the mean of three samples and are standardized to the control at 100. The standard deviation of the mean in all samples was 10% or lower.
Figure 6B:
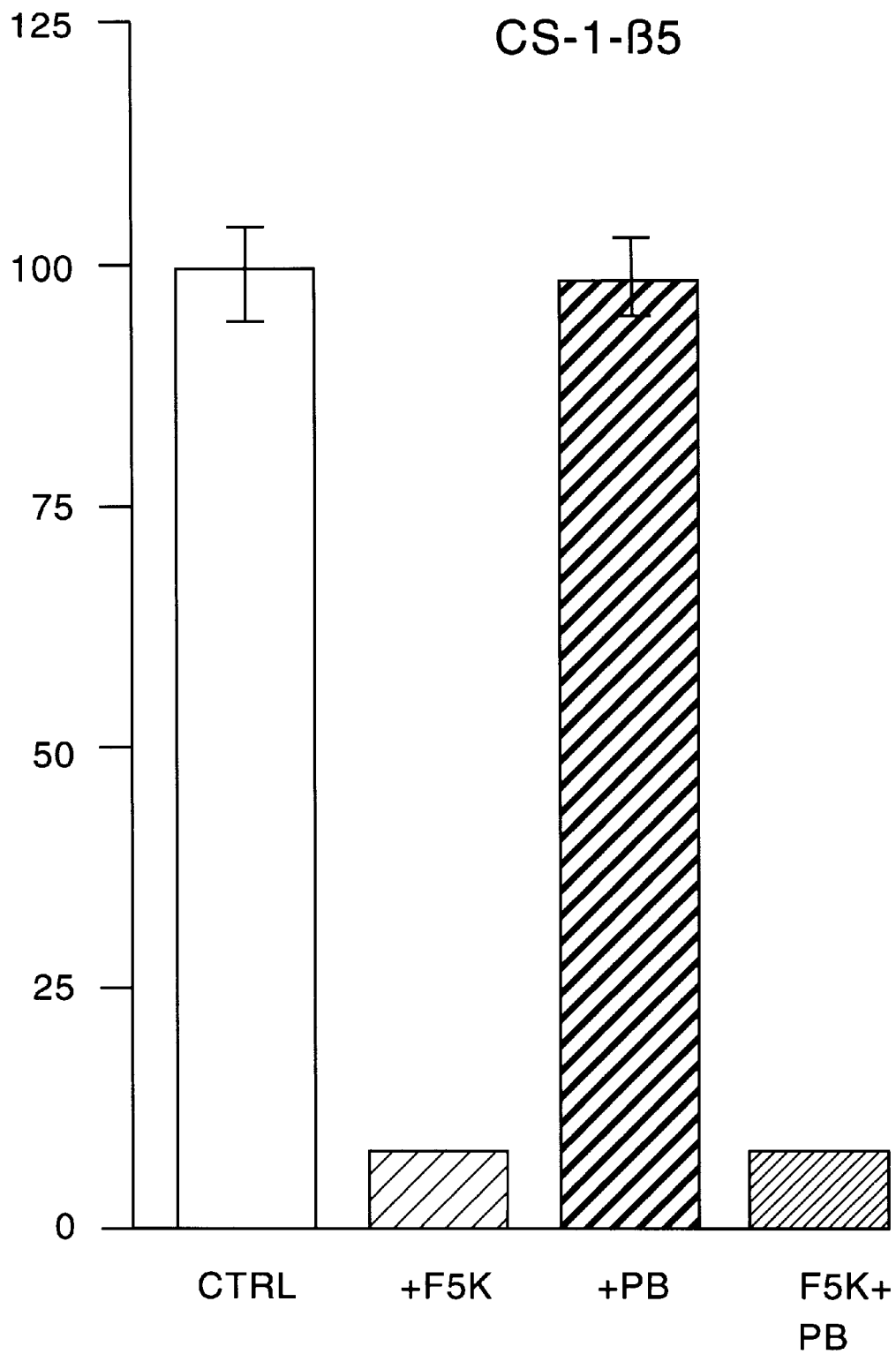
FIG. 6B is a graph of labeled Ad2 binding (% of control) versus CTRL, F5K, PB, and F5K plus PB for CS-1-$\alpha_v\beta5$. Results shown are the mean of three samples and are standardized to the control at 100. The standard deviation of the mean in all samples was 10% or lower.

Binding of Ad2 and Ad9 to the hamster melanoma cell line CS-1, which lacks functional $\alpha_v$ integrins, was also analyzed. One million cells were preincubated with 2 μg/ml of the appropriate fiber knob, 50 μg/ml of Ad2 penton base, or a combination of both and incubated for 1 hr at 4° C. A subsaturating quantity of labeled virus was added and the incubation continued for 1 hr. The cells were then pelleted, washed twice with cold PBS$^{++}$, and counted in a scintillation counter. Ad2 bound to CS-1 as expected, as shown in FIGS. 6A and 6B, which are graphs of labeled Ad2 binding (% of control) versus CTRL, F5K, PB, and F5K plus PB for CS-1 and CS-1-$\alpha_v\beta5$, respectively. Ad2 bound CS-1 well, and preincubation with F5K resulted in 90% competition. Penton base was not involved in binding. Transfection of CS-1 cells with $\alpha_v\beta5$ integrin had no effect on Ad2 binding.

Figure 6C:
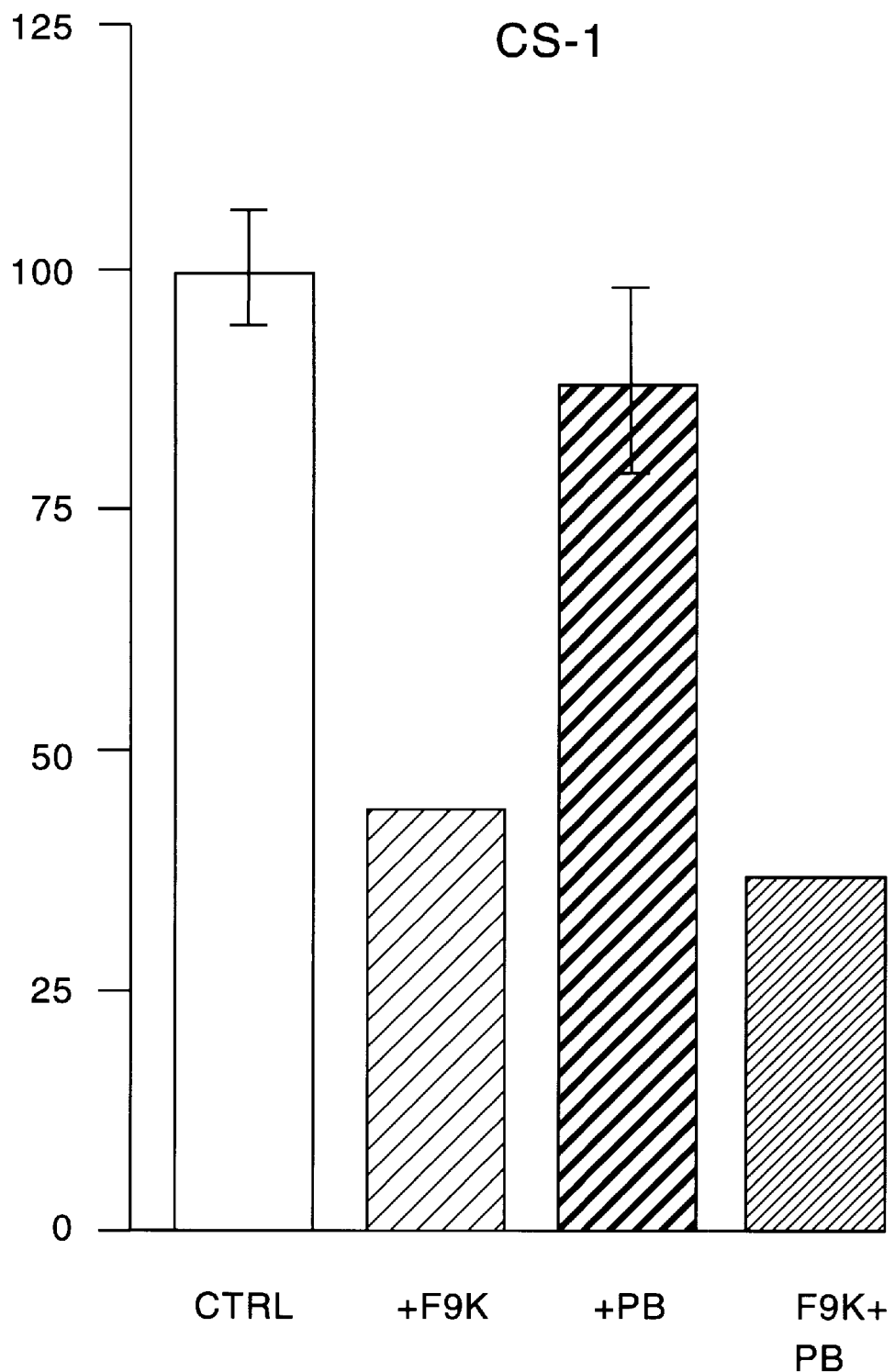
FIG. 6C is a graph of labeled Ad9 binding (% of control) versus CTRL, F9K, PB, and F9K plus PB for CS-1. Results shown are the mean of three samples and are standardized to the control at 100. The standard deviation of the mean in all samples was 10% or lower.
Figure 6D:
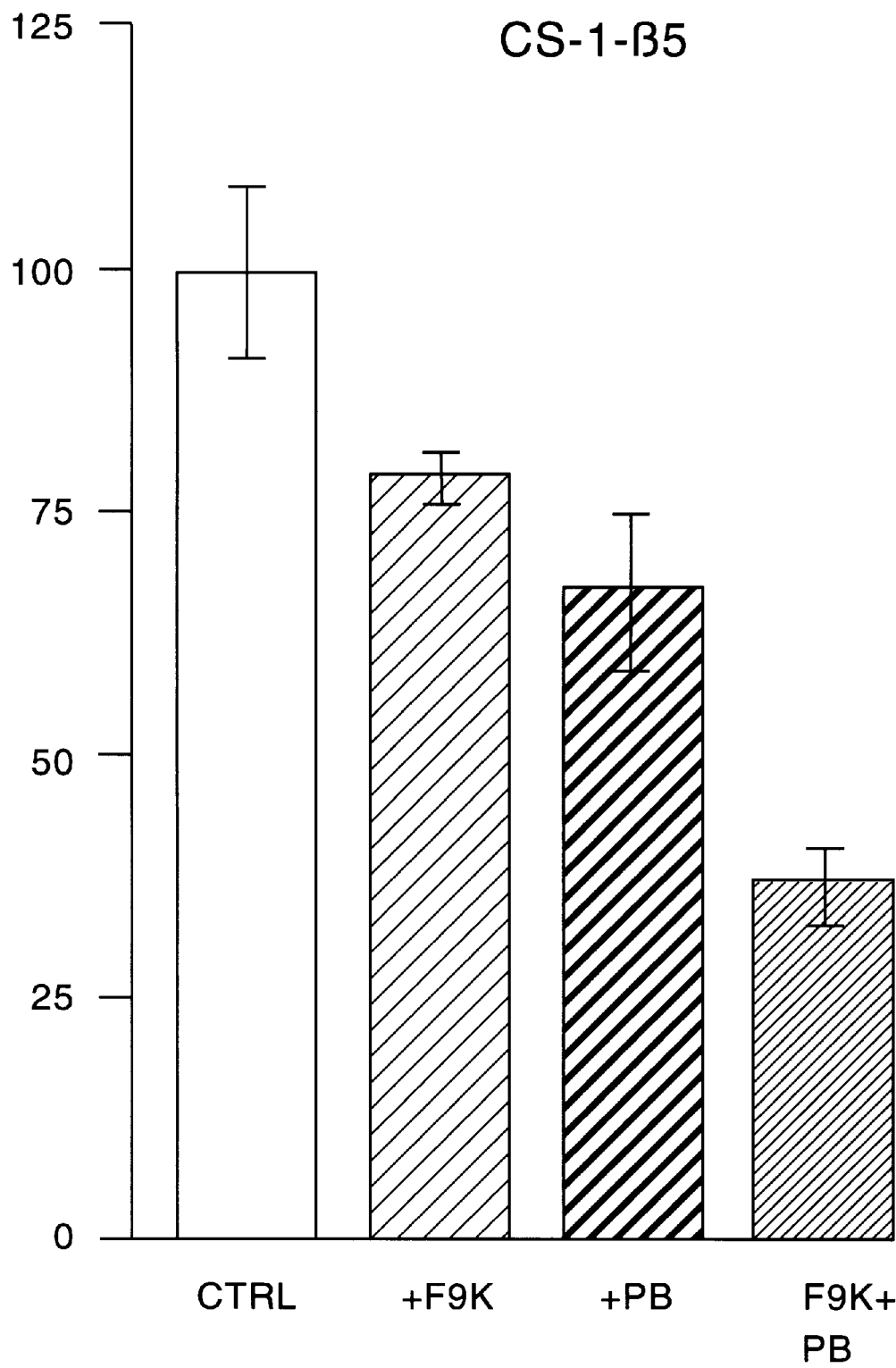
FIG. 6D is a graph of labeled Ad9 binding (% of control) versus CTRL, F9K, PB, and F9K plus PB for CS-1-$\alpha_v\beta5$.

Ad9 bound to CS-1 as shown in FIGS. 6C and 6D, which are graphs of labeled Ad9 binding (% of control) versus CTRL, F9K, PB, and F9K plus PB for CS-1 and CS-1-$\alpha_v\beta5$, respectively. Ad9 bound CS-1 at a level approximately 5 times lower than Ad2, and preincubation with F9K resulted in 65% competition. No significant effect was observed for preincubation with penton base. Unlike Ad2, transfection of CS-1 cells with $\alpha_v\beta5$ integrin, however, dramatically changed the binding characteristics of Ad9. Whereas the total binding of Ad9 increased by a factor of two, preincubation with F9K dropped competition to 25%, preincubation with penton base resulted in a 40% inhibition, and preincubation with F9K and penton base increased inhibition to 65%. Transfection of CS-1 cells with $\alpha_v\beta3$ integrin had a similar but less pronounced effect.

The failure of F9K to block Ad9 binding to many cell lines correlates with the ability of Ad9, unlike Ad2, to bind to cells via $\alpha_v$ integrins independently of fiber. Therefore, $\alpha_v$ integrins can act as second attachment sites for Ad9 virus, which explains why soluble fiber does not block attachment of Ad9 to many cell lines. Preincubation of Hs 700T cells with saturating amounts of penton base and F9K, which blocks 77% of binding by Ad9, indicates that virus-cell interactions other than fiber-receptor and penton-integrin may play a role and, in fact, can at least partially replace these interactions as shown for the FFU analysis of Ad9 infection in Hs 700T cells shown in FIG. 5B. Interaction of penton base with cellular integrins other than $\alpha_v$ integrins and interaction of hexon with cell-surface proteins may explain why Ad9 can apparently bind to and enter cells using a fiber- and $\alpha_v$ integrin-independent mechanism.

Unlike Ad9, preincubation of A549 cells with saturating amounts of the function-neutralizing mAb L230 and F3K completely abrogated labeled Ad3 binding, even though Ad3 has a short fiber (10–11 nm) like Ad9 (12–13 nm). Up to 15% of the binding observed for labeled Ad3, therefore, resulted from direction interaction of the virus with $\alpha_v$ integrins. It appears, therefore, that Ad3, despite having a fiber length comparable to that of Ad9, interacts primarily with its fiber receptor, which must be more readily available than the fiber receptor recognized by Ad2/5/9 fibers.

Example 6

This example describes the construction of the short-shafted viral vector AdSEAP.F5F9Kshort.

The transfer plasmid p193 NS 83-100 was constructed by cloning the Ad5 Nde I to Sal I fragment, which spans the 83-100 map unit region of the Ad5 genome, into the plasmid pNEB193 (New England Biolabs, Beverly, Mass.). The Nde I-Mun I fragment was replaced with a synthetic oligonucleotide comprising a Bam HI site, which was flanked by a 5' Nde I site and a 3' Mun I site to facilitate cloning. The double-stranded synthetic oligonucleotide fragment was created from the overlapping synthetic single-stranded sense and antisense oligonucleotides TATGGA GGAT CCAATAAAGA ATCGTTTGTG TTATGTTTCA ACGTGTTTAT TTTTC (SEQ ID NO: 12) and AAT- TGAAAAA TAAACACGTT GAAACATAAC ACAAAC- GATT CTTTATTGGATCCTCCA (SEQ ID NO: 13). The ends of the overlapping oligomers were made to have overhangs compatible for direct cloning into the Nde I and Mun I sites. The resultant vector p193NS(ΔF) lacked all the coding sequence for the fiber gene but contained the entire adenoviral E4 coding sequence. The plasmid retained the polyadenylation signal, which is shown in bold in SEQ ID NOS: 14 and 15, included in the synthetic Nde I/Mun I oligonucleotide and also incorporated a new Bam HI restriction site, which is shown by underline in SEQ ID NOS: 14 and 15.

The transfer plasmid p193(F5*), which contains a mutated fiber gene with a Bam HI site between the last fiber protein codon and the fiber protein stop codon, was constructed from p193NS(ΔF). The mutated fiber gene was incorporated into the fiber-minus p193NS(ΔF) plasmid using synthetic sense and antisense oligonucleotide primers to amplify the fiber gene by polymerase chain reaction while incorporating a modified Bam HI site following the last codon of the fiber gene to create the mutant fiber gene. This Bam HI site also served to code for the amino acids glycine and serine. The primers used to amplify from the Nde I site to the C-terminal coding regions of the fiber gene from Ad5 genomic DNA were the antisense primer TCCCCCCGGG TCTAGATTAG GATCCTTCTT GGGCAATGTA TGA (stop site in bold; Bam HI site underlined; SEQ ID NO: 14) and the sense primer CGTGTATCCA TATGACACAG A (Nde I site underlined; SEQ ID NO: 15). The PCR product was then cut with Nde I and Bam HI and cloned into the Nde I/Bam HI sites of p193NS(ΔF).

The plasmid p193F5F9K-short was constructed from p193F5*. The oligonucleotide primers GGACTAGTAG CATTTAATAA AAAAGAAGAT AAGCGC (SEQ ID NO: 16) and CCGGATCCTC ATTCTTGGGC GATATAGG (SEQ ID NO: 17) were used to amplify the Ad9 sequence encoding the last shaft repeat and knob from the fiber gene. The PCR product was then purified, using standard techniques, and then digested with the restriction enzymes Nhe I and Bam HI, which allowed cloning of the PCR product into the Nhe I/Bam HI region of the P193(F5*) transfer plasmid.

The transfer plasmid p193 F5F9Kshort, which contains the essential E4 region of adenovirus, was cut with Sal I and transfected into 293 cells, which had been infected 1 hr earlier with the adenoviral vector AdSE.E4Gus, which lacks the E4 region and cannot replicate in 293 cells without the E4 genes. Only when the AdSE.E4Gus DNA recombines with the p193 F5F9K short plasmid DNA to obtain the E4 genes is the vector able to replicate in 293 cells. During this recombination, the newly formed vector also picks up the fiber mutations encoded in the plasmids. Viable recombinant E4+ adenovirus containing the F5F9Kshort fiber chimera were then isolated by plaquing the transfected cell lysates 5 days after transfection. The resultant vector AdSE.F5F9Kshort was isolated and purified by standard virological techniques by using two successive rounds of plaquing on 293 cells. The vector was verified to contain the correct insert by PCR and restriction analysis of viral DNA. Oligonucleotide primers, which prime on either side of the fiber gene, showed that the PCR product was of the correct size for a shortened chimeric fiber gene. Restriction analysis of the vector DNA showed that the new vector contained the correct restriction sites that are unique to the Ad9 fiber knob. Accordingly, the p193 F5F9K-short plasmid, a map of which is shown in FIG. 7, encodes a chimeric fiber protein with a short shaft consisting of the first eight β repeats, i.e., 1–8, from Ad5 fiber and the last β repeat from Ad9 fiber for a total of 9 shaft repeat units. In other words, the Ad5 fiber gene was deleted from the Nhe I restriction site of Ad5 fiber to the end of the coding sequence for Ad5 fiber, and the deleted sequence was replaced with Ad9 fiber sequence encoding the knob and the last shaft repeat.

Example 7

This example demonstrates the specificity of alkaline phosphatase gene delivery to 293 cells by AdSE.F5F9Kshort.

293 Cells were incubated in suspension in 0.3 ml DMEM containing 3 μg/ml Ad9 fiber, 50 μg/ml penton base, a combination of fiber and penton base, or no competitor for 45 min at 37° C. Equal amounts of AdSE.F5F9Kshort were then added to each sample, and the samples were incubated for 60 min at 37° C. The cells were then washed three times and cultured at 37° C. for 1 day. The medium was then assayed for secretory alkaline phosphatase activity using an alkaline phosphatase kit according to the manufacturer's directions. The results are shown in FIG. 8, which is a bar graph of alkaline phosphatase expression (RLU) versus control, fiber, PB, and fiber plus PB. Concentrations of recombinant fiber protein, which block 95–99% of gene delivery by adenoviral vectors containing a long-shafted fiber protein, had only a marginal effect on gene delivery by AdSE.F5F9Kshort. However, penton base, which has only a marginal effect on gene delivery by long-shafted Ad5 vectors, decreased delivery by AdSE.F5F9Kshort by over 95%. These results demonstrate that the penton base commands delivery of genes to cells by AdSe.F5F9Kshort, whereas the fiber protein commands delivery of genes to cells by long-shafted Ad2 and Ad5 vectors.

Example 8

This example compares gene delivery to smooth muscle cells by AdSE (long-shafted) and AdSE.F5F9Kshort (short-shafted).

Human intestinal smooth muscle cells, which express little, if any, functional fiber receptor for Ad2, Ad5 or Ad9, were plated in 24 well plates 1 day prior to the experiment. The cells were then incubated in 0.3 ml DMEM with or without 50 μg/ml penton base protein for 1 hr at 37° C. AdSE or AdSE.F5F9Kshort was then added to the cells, and the cells were rocked at room temperature for 1 hr. The cells were then washed three times and cultured at 37° C. for 1 day. The medium was then assayed for secretory alkaline phosphatase activity using an alkaline phosphatase kit according to the manufacturer's directions. The results are shown in FIG. 9, which is a bar graph of alkaline phosphatase expression (RLU) versus control and the competitors penton and mock for AdSe.F5F9Kshort (■) and AdSe (□). These results demonstrate that AdSE.F5F9Kshort is more efficient at delivering genes to certain cell types than AdSE. Furthermore, given that penton base blocked the transduction of the cells, these results indicate that the penton base of AdSE.F5F9Kshort mediates binding and transduction.

All references cited herein are hereby incorporated by reference to the same extent as if each reference were individually and specifically indicated to be incorporated by reference and were set forth in its entirety herein.

While this invention has been described with emphasis upon preferred embodiments, it will be obvious to those of ordinary skill in the art that the preferred embodiments can be varied. It is intended that the invention may be practiced otherwise than as specifically described herein. Accordingly, this invention includes all modifications encompassed within the spirit and scope of the appended claims.

What is claimed is:

1. A recombinant adenovirus comprising (a) a short-shafted fiber and (b) a nonnative gene that is expressed in a cell to which the recombinant adenovirus attaches or by which the recombinant adenovirus is internalized.

2. The recombinant adenovirus of claim 1, wherein said short-shafted fiber comprises a tail, a shaft comprising no more than about twelve β repeats, and a knob.

3. The recombinant adenovirus of claim 2, wherein said shaft and said knob are of the same serotype.

4. The recombinant adenovirus of claim 3, wherein said serotype is selected from the group consisting of Ad2 and Ad5.

5. The recombinant adenovirus of claim 2, wherein said shaft and said knob are of different serotypes.

6. The recombinant adenovirus of claim 5, wherein said serotypes are from different subgroups of adenovirus selected from the group consisting of C and D.

7. The recombinant adenovirus of claim 5, wherein said serotype of said knob is selected from the group consisting of Ad2 and Ad5.

8. The recombinant adenovirus of claim 5, wherein said knob is of the same serotype as that of the penton base of said recombinant adenovirus.

9. The recombinant adenovirus of claim 2, wherein said shaft is a portion of a shaft, wherein said portion is that which is adjacent to a tail in a fiber of a naturally occurring adenovirus.

10. The recombinant adenovirus of claim 2, which additionally comprises a nonnative amino acid sequence in addition to or in place of a native penton base amino acid sequence or a native fiber knob amino acid sequence, wherein said nonnative amino acid sequence does not prevent assembly of said adenovirus.

11. The recombinant adenovirus of claim 10, wherein said nonnative amino acid sequence is a cellular receptor binding sequence.

12. The recombinant adenovirus of claim 10, wherein said nonnative amino acid sequence is a bispecific or multispecific protein binding sequence.

13. The recombinant adenovirus of claim 12, wherein said bispecific or multispecific protein binding sequence is an antibody binding site.

14. The recombinant adenovirus of claim 10, wherein said nonnative amino acid sequence is located in the penton base.

15. The recombinant adenovirus of claim 10, wherein said nonnative amino acid sequence is located in an exposed loop of said knob.

16. The recombinant adenovirus of claim 10, wherein said nonnative amino acid sequence is an extension of the C-terminus of said knob.

17. A recombinant baculovirus comprising a short-shafted adenoviral fiber gene, wherein said gene encodes a short-shafted adenoviral fiber protein comprising a tail, a shaft, and a knob.

18. A short-shafted adenoviral fiber comprising a tail, a shaft, and a knob.

19. A viral transfer vector comprising a short-shafted adenoviral fiber gene, wherein said gene encodes a short-shafted adenoviral fiber protein comprising a tail, a shaft, and a knob.

20. The viral transfer vector of claim 19, wherein said viral transfer vector is an adenoviral transfer vector.

21. A prokaryotic or eukaryotic expression vector comprising a short-shafted adenoviral fiber gene, wherein said gene encodes a short-shafted adenoviral fiber protein comprising a tail, a shaft, and a knob.

22. A method of targeting attachment of an adenovirus to a cell to effect cell entry of the adenovirus in vitro, which method comprises contacting the cell with the adenovirus of claim 1 such that entry of said adenovirus into said cell is effected.

23. A method of targeting attachment of an adenovirus to a cell to effect cell entry of the adenovirus in vitro, which method comprises contacting the cell with the adenovirus of claim 2 such that entry of said adenovirus into said cell is effected.

24. A method of targeting attachment of an adenovirus to a cell to effect cell entry of the adenovirus in vitro, which method comprises contacting the cell with the adenovirus of claim 10 such that entry of said adenovirus into said cell is effected.

25. The recombinant adenovirus of claim 1, wherein said short-shafted fiber comprises a tail, a shaft, and a knob, and said shaft and said knob are of the same serotype.

26. The recombinant adenovirus of claim 25, wherein said serotype is selected from the group consisting of Ad2 and Ad5.

27. A method of targeting attachment of an adenovirus to a cell to effect cell entry of the adenovirus in vitro, which method comprises contacting the cell with the adenovirus of claim 25 such that entry of said adenovirus into said cell is effected.

28. The recombinant adenovirus of claim 1, wherein said short-shafted fiber comprises a tail, a shaft, and a knob, and wherein said shaft and said knob are of different serotypes.

29. The recombinant adenovirus of claim 28, wherein said serotypes are from different subgroups of adenovirus selected from the group consisting of C and D.

30. The recombinant adenovirus of claim 28, wherein said serotype of said knob is selected from the group consisting of Ad2 and Ad5.

31. The recombinant adenovirus of claim 28, wherein said knob is of the same serotype as that of the penton base of said recombinant adenovirus.

32. A method of targeting attachment of an adenovirus to a cell to effect cell entry of the adenovirus in vitro, which method comprises contacting the cell with the adenovirus of claim 28 such that entry of said adenovirus into said cell is effected.

33. The recombinant adenovirus of claim 1, wherein said short-shafted fiber comprises a tail, a portion of a shaft, and a knob, and wherein said portion is that which is adjacent to a tail in a fiber of a naturally occurring adenovirus.

34. The recombinant adenovirus of claim 1, which additionally comprises a nonnative amino acid sequence in addition to or in place of a native penton base amino acid sequence or a native fiber knob amino acid sequence, wherein said nonnative amino acid sequence does not prevent assembly of said adenovirus.

35. The recombinant adenovirus of claim 34, wherein said nonnative amino acid sequence is a cellular receptor binding sequence.

36. The recombinant adenovirus of claim 34, wherein said nonnative amino acid sequence is a bispecific or multispecific protein binding sequence.

37. The recombinant adenovirus of claim 36, wherein said bispecific or multispecific protein binding sequence is an antibody binding site.

38. The recombinant adenovirus of claim 34, wherein said nonnative amino acid sequence is located in the penton base.

39. The recombinant adenovirus of claim 34, wherein said nonnative amino acid sequence is located in an exposed loop of said knob.

40. The recombinant adenovirus of claim 34, wherein said nonnative amino acid sequence is an extension of the C-terminus of said knob.

41. A method of targeting attachment of an adenovirus to a cell to effect cell entry of the adenovirus in vitro, which method comprises contacting the cell with the adenovirus of claim 34 such that entry of said adenovirus into said cell is effected.

42. The recombinant adenovirus of claim 1, wherein said adenovirus has a penton base that commands cell binding.

43. A method of targeting attachment of an adenovirus to a cell to effect cell entry of the adenovirus in vitro, which method comprises contacting the cell with the adenovirus of claim 42 such that entry of said adenovirus into said cell is effected.

44. The recombinant adenovirus of claim 1, wherein said adenovirus binds to a cell, and wherein said binding of said adenovirus to said cell is not substantially diminished in the presence of said short-shafted fiber apart from any adenovirus.

45. The recombinant adenovirus of claim 44, wherein said binding of said adenovirus to said cell is diminished less than 5% in the presence of said short-shafted fiber apart from any adenovirus.

46. The recombinant adenovirus of claim 45, wherein said adenovirus is of subgroup C.

47. A method of targeting attachment of an adenovirus to a cell to effect cell entry of the adenovirus in vitro, which method comprises contacting the cell with the adenovirus of claim 44 such that entry of said adenovirus into said cell is effected.

48. A method of targeting attachment of an adenovirus to a cell to effect cell entry of the adenovirus in vitro, which method comprises contacting the cell with the adenovirus of claim 45 such that entry of said adenovirus into said cell is effected.

49. A method of targeting attachment of an adenovirus to a cell to effect cell entry of the adenovirus in vitro, which method comprises contacting the cell with the adenovirus of claim 46 such that entry of said adenovirus into said cell is effected.

50. The recombinant adenovirus of claim 1, wherein said adenovirus is not targeted to a cell through said short-shafted fiber.

51. The recombinant adenovirus of claim 50, wherein said cell comprises a cell surface receptor to which said short-shafted fiber binds when said short-shafted fiber is apart from any adenovirus.

52. The recombinant adenovirus of claim 51, wherein said adenovirus is of subgroup C.

53. A method of targeting attachment of an adenovirus to a cell to effect cell entry of the adenovirus in vitro, which method comprises contacting the cell with the adenovirus of claim 50 such that entry of said adenovirus into said cell is effected.

54. A method of targeting attachment of an adenovirus to a cell to effect cell entry of the adenovirus in vitro, which method comprises contacting the cell with the adenovirus of claim 51 such that entry of said adenovirus into said cell is effected.

55. A method of targeting attachment of an adenovirus to a cell to effect cell entry of the adenovirus in vitro, which method comprises contacting the cell with the adenovirus of claim 52 such that entry of said adenovirus into said cell is effected.

56. The recombinant adenovirus of claim 1, wherein said adenovirus is of subgroup C.

57. A method of targeting attachment of an adenovirus to a cell to effect cell entry of the adenovirus in vitro, which method comprises contacting the cell with the adenovirus of claim 56 such that entry of said adenovirus into said cell is effected.

58. A method of targeting attachment of the adenovirus of claim 12 to a cell to effect cell entry in vitro, which method comprises:

(a) contacting said adenovirus with a bispecific or multi-specific binding agent comprising (i) a first component that selectively binds the bispecific or multispecific protein binding sequence, respectively, in said adenovirus, and (ii) a second component that selectively binds a cell surface binding site on said cell, so as to form a complex of said adenovirus and said bispecific or multispecific binding agent; and (b) contacting said cell with the complex of (a) such that entry of said adenovirus into said cell is effected.

59. The method of claim 58, wherein said bispecific or multispecific protein binding sequence is an antibody binding site and said bispecific or multispecific binding agent is an antibody.

60. A method of targeting attachment of the adenovirus of claim 36 to a cell to effect cell entry in vitro, which method comprises:

(a) contacting said adenovirus with a bispecific or multi-specific binding agent comprising (i) a first component that selectively binds the bispecific or multispecific protein binding sequence, respectively, in said adenovirus, and (ii) a second component that selectively binds a cell surface binding site on said cell, so as to form a complex of said adenovirus and said bispecific or multispecific binding agent; and (b) contacting said cell with the complex of (a) such that entry of said adenovirus into said cell is effected.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Lys Gln Ala Gly Asp
  1           5

(2) INFORMATION FOR SEQ ID NO:2:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Glu Ile Leu Asp Val
  1           5

(2) INFORMATION FOR SEQ ID NO:3:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:3:

-continued

```
    Asn Pro Xaa Tyr
    1
```

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
    Glu Asp Pro Gly Phe Phe Asn Val Glu
    1               5
```

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
    Glu Pro Gly Lys Gln Leu Tyr Asn Val Glu
    1               5                   10
```

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
    Lys Lys Lys Lys Lys
    1               5
```

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
    Arg Arg Arg Arg Arg
    1               5
```

(2) INFORMATION FOR SEQ ID NO:8:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
    Asp Tyr Lys Asp Asp Asp Asp Lys
    1               5
```

(2) INFORMATION FOR SEQ ID NO:9:

(i) SEQUENCE CHARACTERISTICS:
       (A) LENGTH: 26 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:9:

```
    Thr Ser Glu Ala Ala Ala His Ala Ile Arg Gly Asp Thr Tyr Ala Asp
    1               5                   10                  15

Tyr Lys Asp Asp Asp Asp Lys Gly Ser Ser
                20                  25
```

(2) INFORMATION FOR SEQ ID NO:10:

(i) SEQUENCE CHARACTERISTICS:
       (A) LENGTH: 25 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:10:

```
    Thr Ser Glu Ala Ala Ala His Ala Ile Arg Gly Asp Thr Tyr Pro Tyr
    1               5                   10                  15

Asp Val Pro Asp Tyr Ala Gly Ser Ser
                20                  25
```

(2) INFORMATION FOR SEQ ID NO:11:

(i) SEQUENCE CHARACTERISTICS:
       (A) LENGTH: 9 amino acids
       (B) TYPE: amino acid
       (C) STRANDEDNESS: single
       (D) TOPOLOGY: unknown (ii) MOLECULE TYPE: peptide (xi) SEQUENCE DESCRIPTION: SEQ ID NO:11:

```
    Tyr Pro Tyr Asp Val Pro Asp Tyr Ala
    1               5
```

(2) INFORMATION FOR SEQ ID NO:12:

(i) SEQUENCE CHARACTERISTICS:
       (A) LENGTH: 55 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO:12:

```
TATGGAGGAT CCAATAAAGA ATCGTTTGTG TTATGTTTCA ACGTGTTTAT TTTTC          55
```

(2) INFORMATION FOR SEQ ID NO:13:

(i) SEQUENCE CHARACTERISTICS:
       (A) LENGTH: 57 base pairs
       (B) TYPE: nucleic acid
       (C) STRANDEDNESS: single
       (D) TOPOLOGY: linear -continued (ii) MOLECULE TYPE: DNA (synthetic)

(xi) SEQUENCE DESCRIPTION: SEQ ID NO:13:

AATTGAAAAA TAAACACGTT GAAACATAAC ACAAACGATT CTTTATTGGA TCCTCCA        57

(2) INFORMATION FOR SEQ ID NO:14:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:14:

TCCCCCCGGG TCTAGATTAG GATCCTTCTT GGGCAATGTA TGA        43

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:15:

CGTGTATCCA TATGACACAG A        21

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:16:

GGACTAGTAG CATTTAATAA AAAAGAAGAT AAGCGC        36

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:17:

CCGGATCCTC ATTCTTGGGC GATATAGG        28